United States Patent
Pacifici et al.

(10) Patent No.: US 9,285,314 B2
(45) Date of Patent: Mar. 15, 2016

(54) SYSTEMS AND METHODS ENABLING HIGH-THROUGHPUT, REAL TIME DETECTION OF ANALYTES

(71) Applicant: Brown University, Providence, RI (US)

(72) Inventors: Domenico Pacifici, Providence, RI (US); Henri J. Lezec, Bethesda, MD (US); Tayhas G. r. Palmore, Providence, RI (US); Vince Siu, Thornhill (CA); Vihang Mehta, Pune (IN); Alec Roelke, Basking Ridge, NJ (US); Steve Rhieu, Rockville, MD (US); Jing Feng, Jiangsu (CN)

(73) Assignee: Brown University, Providence, RI (US)

( * ) Notice: Subject to any disclaimer, the term of this patent is extended or adjusted under 35 U.S.C. 154(b) by 0 days.

(21) Appl. No.: 14/350,896

(22) PCT Filed: Oct. 12, 2012

(86) PCT No.: PCT/US2012/060079
§ 371 (c)(1),
(2) Date: Apr. 10, 2014

(87) PCT Pub. No.: WO2013/056137
PCT Pub. Date: Apr. 18, 2013

(65) Prior Publication Data
US 2014/0327913 A1   Nov. 6, 2014

Related U.S. Application Data

(60) Provisional application No. 61/662,048, filed on Jun. 20, 2012, provisional application No. 61/581,951, filed on Dec. 30, 2011, provisional application No. 61/546,435, filed on Oct. 12, 2011.

(51) Int. Cl.
*G01B 9/02* (2006.01)
*G01N 21/552* (2014.01)
*G01N 21/45* (2006.01)

(52) U.S. Cl.
CPC .............. *G01N 21/553* (2013.01); *G01N 21/45* (2013.01); *G01N 21/554* (2013.01)

(58) Field of Classification Search
CPC .............. G01B 9/02; G01J 11/00; G01J 9/02; G01J 9/0246; G01N 21/45
USPC ......................................... 356/450
See application file for complete search history.

(56) References Cited

U.S. PATENT DOCUMENTS 6,653,152 B2   11/2003 Challener
7,031,562 B2 *   4/2006 Paddon et al. .................. 385/14
(Continued)

OTHER PUBLICATIONS

Chan et al., "Transmission Enhancement in an Array of Subwavelength Slits in Aluminum Due to Surface Plasmon Resonances," Bell Labs Technical Journal, vol. 10, No. 3, No Month Listed 2005 (pp. 143-150).

(Continued)

*Primary Examiner* — Tarifur Chowdhury
*Assistant Examiner* — MD Rahman
(74) *Attorney, Agent, or Firm* — Wilmer Cutler Pickering Hale and Dorr LLP

(57) ABSTRACT

System and methods for detecting analytes are provided. The system includes a plasmonic interferometer with a first surface having a first and second scattering element and an aperture disposed between the first scattering element and the second scattering element. A first distance between the aperture and the first scattering element and a second distance between the aperture and the second scattering element are selected to provide interference of light at the slit. The system also includes a light source for illuminating the first surface of the plasmonic interferometer, a detector positioned for detecting light transmitted through the aperture, and a sample holder for disposing a sample to be analyzed onto the first surface of the plasmonic interferometer.

42 Claims, 24 Drawing Sheets

(56) References Cited

U.S. PATENT DOCUMENTS

| | | | |
|---|---|---|---|
| 7,518,737 B2 | 4/2009 | Hall et al. | |
| 7,864,313 B2 | 1/2011 | Baumberg et al. | |
| 8,094,314 B2 | 1/2012 | Tetz et al. | |
| 8,120,783 B2 | 2/2012 | Li | |
| 8,649,014 B2 | 2/2014 | Gan et al. | |
| 2003/0143580 A1* | 7/2003 | Straus | 435/6 |
| 2004/0018127 A1* | 1/2004 | Long et al. | 422/186.04 |
| 2004/0046128 A1* | 3/2004 | Abel et al. | 250/458.1 |
| 2004/0218184 A1 | 11/2004 | Jorgenson et al. | |
| 2006/0244969 A1* | 11/2006 | Ryan et al. | 356/446 |
| 2007/0107103 A1 | 5/2007 | Kempa et al. | |
| 2008/0119701 A1* | 5/2008 | Milner et al. | 600/342 |
| 2008/0186500 A1* | 8/2008 | Schmidt et al. | 356/450 |
| 2008/0212102 A1 | 9/2008 | Nuzzo et al. | |
| 2009/0273532 A1* | 11/2009 | Mendis et al. | 343/753 |
| 2010/0102256 A1* | 4/2010 | Andrew et al. | 250/505.1 |
| 2010/0256016 A1 | 10/2010 | Blair et al. | |
| 2010/0271634 A1 | 10/2010 | Dominguez Horna et al. | |
| 2011/0080589 A1 | 4/2011 | Gan et al. | |
| 2011/0157592 A1 | 6/2011 | Tsao et al. | |
| 2011/0310394 A1 | 12/2011 | Li | |
| 2012/0026509 A1 | 2/2012 | Cui et al. | |
| 2012/0039560 A1* | 2/2012 | Mazur et al. | 385/2 |
| 2013/0148194 A1* | 6/2013 | Altug et al. | 359/350 |

OTHER PUBLICATIONS

Genet et al., "Light in Tiny Holes," Nature, vol. 445, Jan. 4, 2007 (pp. 39-46).

International Search Report and Written Opinion Issued by the U.S. Patent and Trademark Office as International Searching Authority for International Application No. PCT/US2012/60079 mailed Jan. 9, 2013 (11 pgs).

Lee et al., "Sensitive Biosensor Array Using Surface Plasmon Resonance on Metallic Nanoslits," Journal of Biomedical Optics, vol. 12, No. 4, Jul./Aug. 2007 (pp. 044023-1-044023-5).

Leong et al., "Surface Plasmon Resonance in Nanostructured Metal Films under the Kretschmann Configuration," Journal of Applied Physics, vol. 106, No Month Listed 2009 (pp. 124314-1-124314-5).

Perney et al., "Tuning Localized Plasmons in Nanostructured Substrates for Surface-Enhanced Raman Scattering," Optical Society of America, No Month Listed 2005 (11 pages).

Tanemura et al., "Multiple-Wavelength Focusing of Surface Plasmons with a Nonperiodic Nanoslit Coupler," Nano Letters, vol. 11, No Month Listed 2011 (pp. 2693-2698).

Zayats et al., "Nano-Optics of Surface Plasmon Polaritons," Physics Reports, vol. 408, No Month Listed 2005 (pp. 131-314).

* cited by examiner

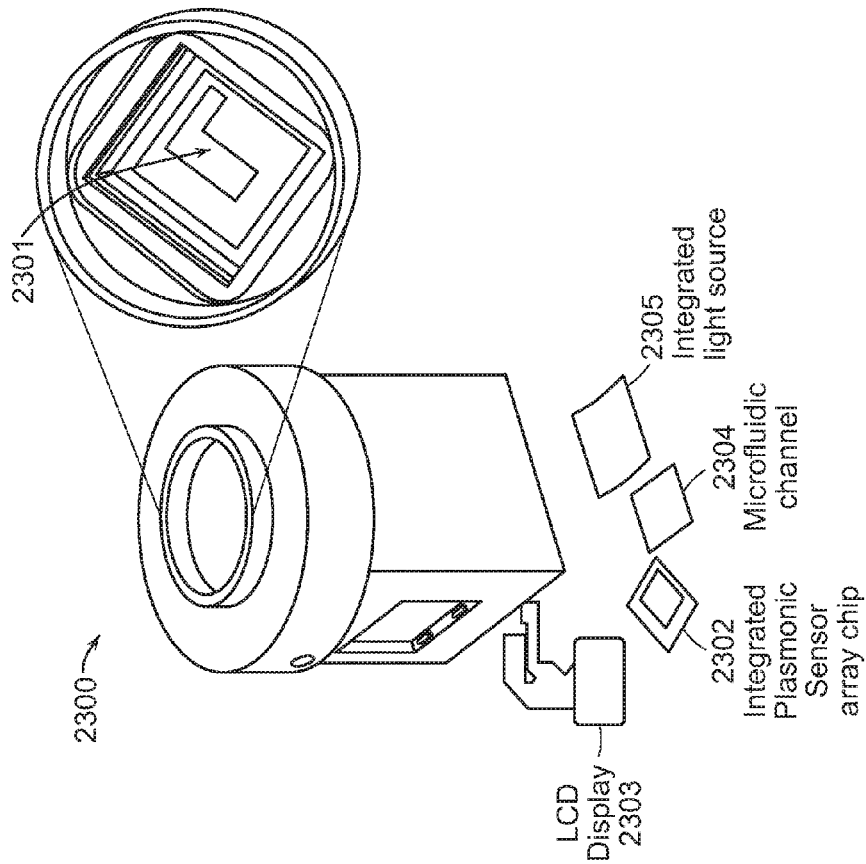
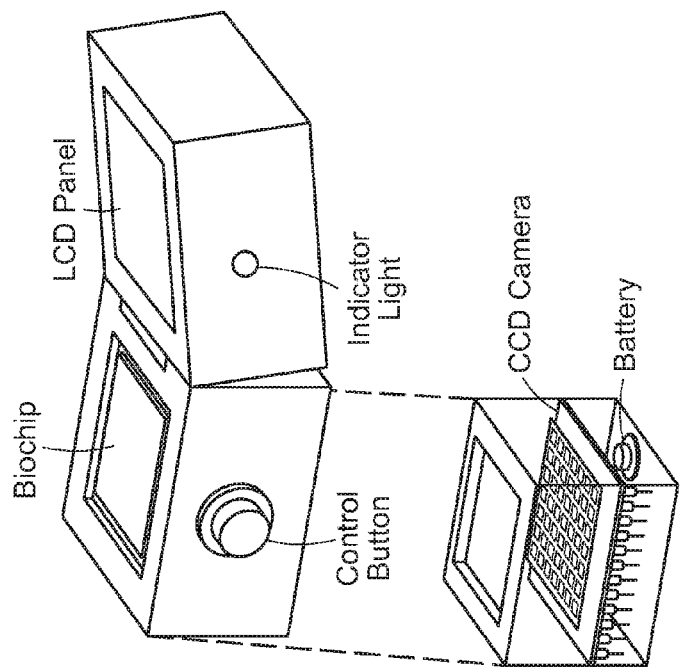
FIG. 23B
FIG. 23A

SYSTEMS AND METHODS ENABLING HIGH-THROUGHPUT, REAL TIME DETECTION OF ANALYTES

CROSS-REFERENCE TO RELATED APPLICATION

This application is a national stage application of International Application No. PCT/US12/60079, filed on Oct. 12, 2012, entitled "SYSTEMS AND METHODS ENABLING HIGH-THROUGHPUT, REAL TIME DETECTION OF ANALYTES," incorporated herein by reference in its entirety, which claims priority under 35 U.S.C. §119(e) to U.S. Provisional Application No. 61/662,048, filed on Jun. 20, 2012, entitled "ENHANCING THE SENSITIVITY AND SELECTIVITY OF PLASMONIC INTERFEROMETERS USING DYE CHEMISTRY," which is incorporated herein by reference in its entirety which is incorporated herein by reference in its entirety. This application also claims priority under 35 U.S.C. §119(e) to U.S. Provisional Application No. 61/581,951, filed on Dec. 30, 2011, entitled "NANOSCALE PLASMONIC INTERFEROMETERS FOR MULTISPECTRAL, HIGH-THROUGHPUT BIOCHEMICAL SENSING," which is incorporated herein by reference in its entirety. This application also claims priority under 35 U.S.C. §119(e) to U.S. Provisional Application No. 61/546,435, filed on Oct. 12, 2011, entitled "SYSTEMS AND METHODS ENABLING HIGH-THROUGHPUT, REAL TIME DETECTION OF BIOCHEMICAL ANALYTES," which is incorporated herein by reference in its entirety.

BACKGROUND

The invention is generally directed to systems and methods for high-throughput, real-time detection of analytes in fluids, for example, bodily fluids (e.g. cytokines in blood, glucose in saliva, tears and blood, etc.).

Current detection and screening techniques use low throughput, highly selective, non-scalable methods, which require labeling of the target molecule with a fluorophore to tag the specific molecule under study. These methods have several drawbacks: (1) prior knowledge of the molecule to be sensed is necessary, (2) modification of its structure is often needed to incorporate the tag, and (3) the tag molecule can change the way the primary molecule binds to other molecules, reducing the accuracy of an assay. Under alternative aspects of the present disclosure, label-free sensing is achieved using surface plasmon resonance (SPR) in thin metal films functionalized with specific linkers to selectively capture the analyte to be detected.

Typical SPR implementations rely on a prism or metallic grating (such as groove, slit and hole arrays) to couple the incident beam into propagating surface plasmon polaritons (SPPs), using light incident at a wavelength-specific angle. Also widely used are localized surface plasmon resonances (L-SPRs) in metal nanoparticles producing resonant scattering and extinction at specific frequencies. Given the resonant nature of the SPP excitation, practical implementations of SPR-based sensing schemes are limited in the number and range of wavelengths that can be used to sense the presence of analytes, thus further limiting their spectroscopic capabilities. Furthermore, SPR-based systems require large-volume samples and are limited to the detection of chemicals one at a time.

The dispersion relation of SPP waves shows longer wave vectors compared to electromagnetic waves traveling in dielectric materials (See FIG. 1a). This is why light incident upon a flat metal surface cannot excite surface plasmon polaritons directly (See FIG. 1b).

According to aspects of the present disclosure, excitation of SPP waves can be achieved by nano-corrugations, patterned on a flat metal surface (See FIGS. 1c-e), for example, grooves, slits, holes, or any surface plasmon launcher, which is any structure that can act as a SPP localized source.

FIG. 2a shows a commercially available Surface Plasmon Resonance (SPR) biochip. By measuring the angular shift of this characteristic band, detection of a refractive index change is accomplished. This approach leads to table-top instruments, where a large sensing area is needed to detect only one specific molecule per measurement session, thus limiting the throughput. Moreover, SPR sensors are monochromatic, in that they typically employ a single illumination wavelength, and they cannot determine the spectral fingerprints of the analyte.

Alternative approaches to label-free detection include fiber-optics, dielectric waveguides, nanowires, biochips, mechanical cantilevers, microring resonators, but none of the previous methods has shown significant throughput capabilities. For example, FIG. 2b shows an ultra high-Q microtoroid sensor.

Label-free detection can also be realized by measuring some optical properties of functionalized noble-metal nanoparticles, such as Surface Enhanced Raman Scattering (SERS), or Mie scattering and light extinction. For example, FIG. 2c shows a nanoscale biosensor. Unfortunately, the detection throughput is strongly limited by the difficulty to reliably address the response of several nanoparticles at once, by the challenging task to achieve uniform coating of all nanoparticles with a linker, and reproducible sensor response.

FIG. 2d shows a typical implementation of SPR, which involves a prism to excite the surface plasmons at the functionalized metal/dielectric interface, which happens when the incident angle is precisely chosen at a specified wavelength. In order to improve throughput, other techniques, such as SPR imaging, have been developed that allow several device cells ($\sim 10^2$) to be used in parallel to image the binding interaction and monitor intensity variations caused by a refractive index change in each cell.

Another method to excite SPR employs metallic gratings (such as hole, slit and groove arrays) as shown in FIGS. 2e-g. This method is based on the idea that the prism is replaced by a periodic array of scatterers etched in a metal film. Excitation of surface plasmons occurs at those resonant wavelengths (or angles, given a specific incident wavelength) satisfying the grating coupling condition. Therefore, reflection and transmission spectra from these devices are also characterized by sharp peaks corresponding to the wavelength- or angle-specific resonant condition. Metal nanoparticles are also widely used, which are characterized by sharp spectroscopic features in their scattering and extinction spectra, so-called localized surface plasmon resonances (LSPRs). Upon binding of the analyte of interest to the functionalized nanoparticle surface, a shift in the peak position of the LSPR is observed and the relative wavelength shift can be used to quantify the amount of analyte adsorbed at the surface. Given the "resonant" nature of the surface plasmon excitation, all the previous approaches involving SPR (prism-, grating-coupled, or localized) are limited in the number of wavelengths that can be used to sense the presence of the analyte. Therefore, the refractive index associated to the analyte can be measured only at one specific wavelength, thus strongly limiting the spectroscopic capabilities of any currently available SPR technique.

According to aspects of the present disclosure, a nanoscale plasmonic interferometer in one manifestation comprises of two grooves flanking a slit in a silver film is provided (see FIG. 2g).

A plasmonic-based device that accurately measures chemical and biological analytes in real-time is provided. Chemical analytes include but are not limited to dielectric materials such as semiconductor quantum dots (QDs) (see FIG. 3a), analytes embedded in thin films, or molecules in a gas or liquid phase. Biological analytes include but are not limited to proteins (e.g. cytokines in blood serum) and small molecules (e.g. glucose in bodily fluids) (see FIG. 3b-d).

In addition to a better understanding of light-matter interaction at the nanoscale, the disclosed methods and systems impact the throughput capabilities of several analyses and assays relevant to human health and currently used in the life sciences, and serve as an alternative high-throughput scheme for faster drug discovery, as well as more efficient identification and screening of novel therapies.

SUMMARY OF THE INVENTION

According to aspects of the present disclosure, a system for detecting an analyte is provided. The system includes a plasmonic interferometer comprising a first surface having a first scattering element and a second scattering element and a aperture disposed between the first scattering element and the second scattering element to define a first distance between the aperture and the first scattering element and a second distance between the aperture and the second scattering element, wherein the first and second distances are selected to provide controlled interference of light at the aperture. The system also includes a light source for illuminating the first surface of the plasmonic interferometer, a detector positioned for detecting light transmitted through the aperture, and a sample holder for disposing a sample to be analyzed onto the first surface of the plasmonic interferometer.

According to alternative aspects of the present disclosure, a method of real-time detection of an analyte is provided. The method includes the steps of providing a plasmonic interferometer, applying a sample to be analyzed on the first surface of the plasmonic interferometer, illuminating the plasmonic interferometer with the light source, measuring a light property of a composite light transmitted through an aperture, and determining a characteristic of an analyte of interest based on the measured light intensity.

According to alternative aspects of the present disclosure, a system for detecting a plurality of analytes includes a plurality of plasmonic interferometers. Each plasmonic interferometer includes a first surface having a first scattering element and a second scattering element and an aperture disposed between the first scattering element and the second scattering element to define a first distance between the aperture and the first scattering element and a second distance between the aperture and the second scattering element. The first and second distances are selected to provide constructive interference of light at the aperture. The system can also include a light source for illuminating the first surface of each of the plurality of plasmonic interferometers, a plurality of detectors positioned for detecting light transmitted through the aperture of each plasmonic interferometer, and a plurality of sample holders, each sample holder disposing a sample to be analyzed onto the first surface of each plasmonic interferometer.

According to alternative aspects of the present disclosure, a system for detecting an analyte includes a plasmonic interferometer, which includes a first surface having a first scattering element and a second scattering element and an aperture disposed between the first scattering element and the second scattering element to define a first distance between the aperture and the first scattering element and a second distance between the aperture and the second scattering element, wherein the first and second distances are selected to provide controlled interference of light at the aperture. The system can also include a light source for illuminating the first surface of the plasmonic interferometer, a detector positioned for detecting light transmitted through the aperture; and a sample holder for disposing a sample to be analyzed onto the first surface of the plasmonic interferometer. The sample can comprise an oxidative or chromogenic dye selected to absorb particular light frequencies.

According to alternative aspects of the present disclosure, a method of real-time detection of an analyte includes the steps of providing a plasmonic interferometer and applying a sample to be analyzed on the first surface of the plasmonic interferometer, wherein the sample comprises an oxidative or chromogenic dye selected to absorb particular light frequencies. The method also includes the steps of illuminating the plasmonic interferometer with the light source, measuring a light property of a composite light transmitted through an aperture, and determining a characteristic of an analyte of interest based on the measured light property.

According to alternative aspects of the present disclosure, a method of spectroscopic measurements of the dispersion relation and optical constants of dielectric materials in gaseous, liquid, or solid form includes the steps of providing a plasmonic interferometer, applying a sample to be analyzed on the first surface of the plasmonic interferometer, wherein the sample comprises at least one of a dielectric materials or a mixture thereof of dielectric material, illuminating the plasmonic interferometer with a light source, measuring a light property of a composite light transmitted through the slit aperture, and determining a characteristic of an analyte of interest in the sample based on the measured light property.

According to aspects of the present disclosure, methods of fabrication of microarrays of plasmonic interferometers are provided, by designing, modeling, fabricating and characterizing metal films patterned according to various periodic, random and quasi-periodic nano-hole, and slit and groove arrays.

According to aspects of the present disclosure, microarrays of plasmonic interferometers are provided, for example, by patterning metal films according to various periodic, random and quasi-periodic nano-hole, and slit and groove arrays.

According to alternative aspects of the present disclosure, methods of development and implementation of surface chemistry by which to attach selective sensing elements for targeted cytokines and glucose are provided.

According to alternative aspects of the present disclosure, methods of device fabrication and optimization for effective cytokine detection in blood serum and glucose detection in saliva are provided.

According to alternative aspects of the present disclosure, devices for effective cytokine detection in blood serum and glucose detection in saliva are provided.

According to alternative aspects of the present disclosure, methods for extraction of fingerprint (dispersion relation) and composition of the analyte are provided.

DESCRIPTION OF THE FIGURES

The following figures are presented for the purpose of illustration only, and are not intended to be limiting:

FIG. 1a is a plot of energy (eV) v. $k_x$ (nm$^{-1}$) showing the surface plasmon dispersion relation for Ag/SiO$_2$, (b) is an illustration of light incident upon a flat metal surface.

FIGS. 1c-e show nanoscale corrugations (e.g. groove, slit and hole) patterned on a flat metal surface that can excite surface plasmon polaritons in counter-propagating directions.

FIGS. 2a-c show a prior art surface plasmon resonance biochip, a microring resonator, and a metal nanoparticle coated with specific linkers, respectively.

FIGS. 2d-g show a prism coupling, grating coupling, groove-slit and groove-slit-groove plasmonic interferometer sensing scheme, respectively, using surface linkers capable of specific binding.

FIGS. 4a-c show SEM micrographs of plasmonic interferometers according to aspects of the present disclosure, in which the plasmonic interferometer includes (a) a single groove/slit arrangement, (b) a two grooves and a slit (GSG) having different groove/slit spacings, $p_1$ and $p_2$, respectively, and (c) a two grooves and a slit (GSG) having different groove/slit spacings, $p_1$ and $p_2$, respectively, (d) is a schematic illustration of a GSG plasmonic interferometer illustrating groove slit distances $p_1$ and $p_2$, (e) shows the light intensity spectra transmitted through an isolated slit and through the slit of a GSG interferometer, and (f) shows the experimental and simulated normalized per-slit transmission spectra.

FIGS. 23a-b show a schematic and a photograph of a prototype plasmonic interferometer, respectively, according to aspects of the present disclosure.

FIG. 24 1-8 illustrates step-by-step instructions to use a self-monitoring glucose meter, according to aspects of the present disclosure.

DETAILED DESCRIPTION OF THE INVENTION

Figure 1:
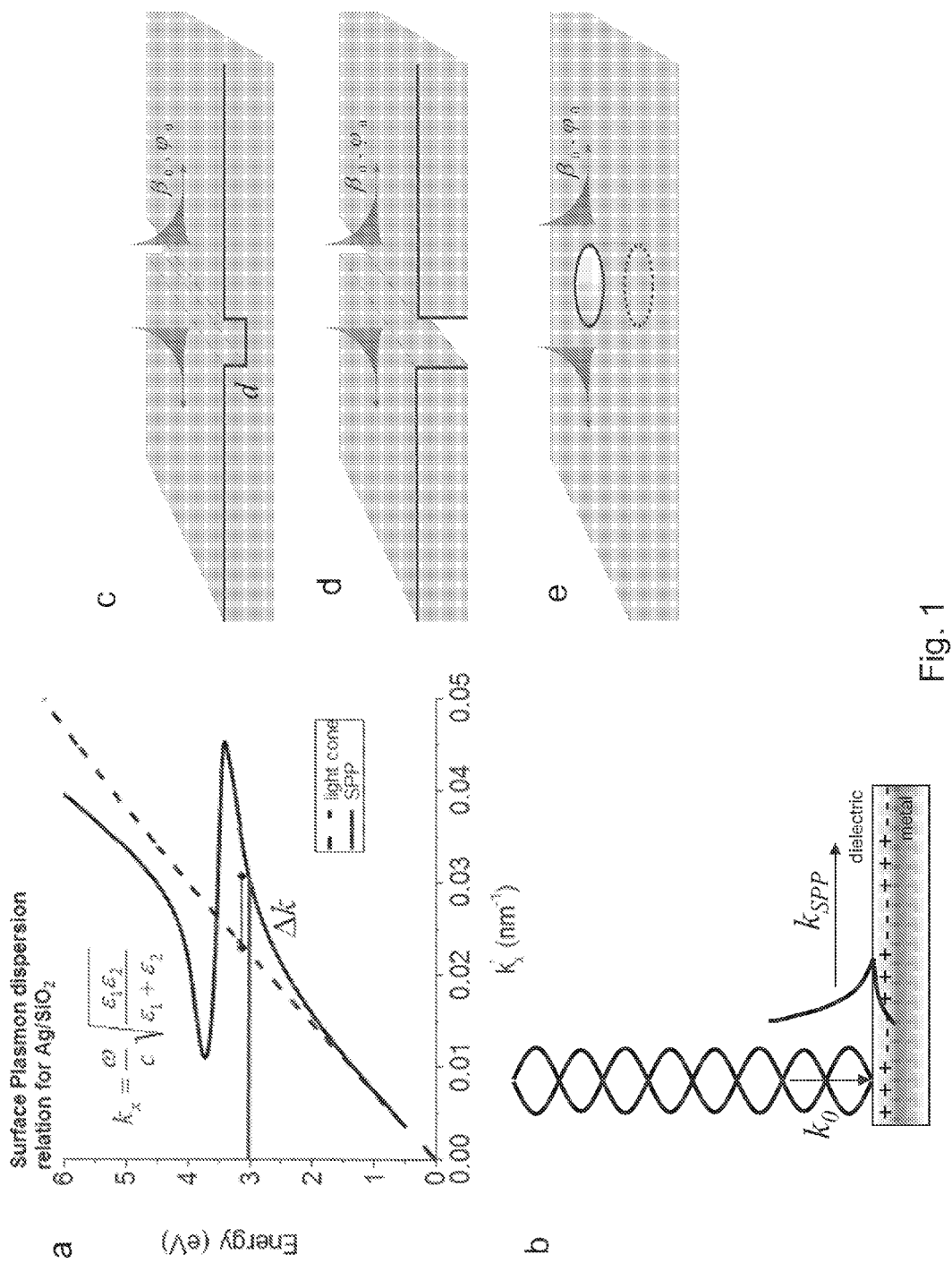

Optical interferometry is a valuable tool used in a variety of areas ranging from astronomy, to fiber optics and biomedical imaging. Typical implementations of optical interferometers employ cavities with dimensions ranging from hundreds of micrometers to meters, such as those used in lasers and optical coherence tomography, and as long as several kilometers, such as those used in the laser interferometer observatory where the existence of gravitational waves (LIGO) has been revealed.

Plasmonics is a rapidly emerging field of nanophotonics enabling the guiding and manipulation of light in devices with a footprint much smaller than the wavelength of the incident light. Plasmonics focuses on the ability of metal nanostructures to manipulate light at the nanoscale. For example, by using nanocorrugations etched in a metal film, light at optical frequencies can be coupled to surface plasmon polaritons (SPPs). SPPs are electromagnetic waves coupled to oscillations of free electrons in a metal. SPPs are guided electromagnetic waves that propagate along a metal dielectric interface with high field confinements at the interface. SPPs are confined at the metal surface and are very sensitive to small changes in the refractive index of the dielectric (e.g., aqueous solutions with analytes).

SPPs are characterized both by maximum field amplitudes at the metal surface and by wavelengths much shorter than the incident wavelength. SPPs have the potential therefore to encode a huge amount of information, indeed larger than in devices with dimensions comparable to or even smaller than modern microelectronic transistors. Moreover, being confined at the metal surface, SPPs are very sensitive to the dielectric properties of the materials on which they propagate. This property allows for increased interaction with light emitters, enhanced field intensities at the surface of metal nanoparticles, extraordinary transmission through periodic hole arrays, higher absorption efficiencies in ultra-thin dielectric layers, as well as superlensing and negative refraction for cloaking applications at visible wavelengths. Moreover, SPPs can be used to sense the presence of chemical and biological analytes. According to aspects of the present disclosure, plasmonic sensors employing interferometry at the micro- and nano-scale are provided for sensing the presence of chemical and biological analytes.

According to aspects of the present disclosure, optical interferometry applications scaled to the nano- and micrometer scale are provided, using novel plasmonic interferometers as the transducers to detect and convert the interaction of an analyte (e.g., cytokines in blood serum, glucose in bodily fluids, etc.) with the sensor surface into a measurable variation of light intensity.

According to aspects of the present disclose, the proposed interferometric approach benefits from the use of surface plasmons that are excited by diffractive scattering of incident light by subwavelength grooves. The proposed sensing scheme can retain the attractiveness of real-time and label-free sensing of conventional SPR.

The nanoscale groove can be used to excite surface plasmons in a broad wavelength range, keeping the angle of incidence constant (for example normal incidence), which constitutes a substantial advantage compared to other grating- and prism-coupling strategies where precise determination and setting of the coupling angle is required for every trial. The proposed method can enable the determination of the refractive index for various analytes as a function of wavelength. Sensitivity of the sensor can be enhanced by simply tuning the incident wavelength or varying the interferometer arm lengths.

According to aspects of the present disclosure, a device based on novel plasmonic architecture can accurately and rapidly measure the level of analytes in a sample in real time. As is demonstrated herein, analytes can be detected at extremely low levels, e.g., at nano-gram, pico-gram and femto-gram levels.

Furthermore, the fundamental science and technology of the disclosed invention can transform to all areas where real-time, sensitive detection of dilute analytes are needed.

The proposed design for plasmonic interferometry is fabricated at the nano scale, employing periodic and quasi-periodic arrays of sub-micrometer scale holes, slits, and grooves (both linear and curvilinear), and can be coupled to surface chemistries that are specific for the analyte of interest. Under aspects of the specific disclosure, a dense microarray of plasmonic interferometers can provide high-throughput, real-time data on analyte levels. In certain aspects, detectors based on plasmonic interferometers can provide high-throughput, real-time data on diluted analytes at low concentrations, such as cytokines in blood serum, glucose in bodily fluids, etc., capabilities not possible with current technology.

According to aspects of the present disclosure, methods of fabrication of microarrays of plasmonic interferometers are provided, by designing, modeling, fabricating and characterizing metal films patterned according to various periodic, random and quasi-periodic nano-hole, slit and groove arrays.

According to aspects of the present disclosure, microarrays of plasmonic interferometers are provided, for example by patterning metal films according to various periodic, random and quasi-periodic nano-hole, and slit and groove arrays.

Detection of extremely dilute chemical and biological species is generally accomplished using low throughput, non-scalable methods that often rely on target labeling to reveal the presence of specific molecules within a single device. Under aspects of the present disclosure, systems and methods are provided for chemical and biological sensing that consists of millions of nano- and micron-scale optical interferometers per centimeter squared, each working as an individually addressable sensor, integrated on a single device.

The detector element is a plasmonic interferometer able to transmit light through a nano-aperture and acting as the transducer. Any variation in analyte levels will determine a change in refractive index and as a consequence the light intensity will vary. Light intensity transmitted through the interferometer will be measured as a function of incident wavelength to determine the spectroscopic fingerprints of the analyte. Moreover, the geometrical parameters can be varied to generate a dense array of such interferometers, working in parallel and individually addressable for high-throughput screening. Scaling the device footprint can be possible using a CCD camera and optical elements. A microprocessor interfacing with the device can perform real-time analysis of the data and display the results.

The microarrays of plasmonic interferometers are prepared using conductive surfaces, such as gold, silver, copper, aluminum, and indium tin oxide and the like. The surfaces can be modified to provide interaction and binding of the analyte of interest using well established methods. Surface chemistries include metal-thiol self-assembled monolayers and subsequent chemical reactions at their end-groups as well as electrodeposited polymers and their subsequent surface modification. Surfaces modified by these chemistries can be used for electrochemical sensing (e.g., vitamin D and glucose detection), bioelectrocatalysis (e.g., oxygen reduction), and cellular communication (e.g., electrically stimulated nerve cell adhesion and neurite extension).

According to aspects of the present disclosure, nanoscale plasmonic interferometers comprising two grooves flanking a slit in a silver film are provided. The two grooves can scatter a normally incident white light beam into multifrequency SPPs, counter-propagating at the metal/dielectric interface. The field amplitudes of the two SPP waves interfere with the incident field at the slit location, thus causing a modulation in the light intensity transmitted through the slit. The transmitted intensity depends on wavelength, refractive index, and it can also be tuned by simply varying the groove-slit separation distances (i.e., the lengths of the two interferometer arms). Since SPPs are strongly confined at the metal/dielectric interface, a far-field measurement of the light intensity transmitted through the slit carries information about the near-field interaction of the SPPs with the dielectric material, useful to determine the refractive index of unknown chemical analytes and their concentration in solution, only a few tens or hundreds of nanometers above the metal surface. Furthermore, SPPs can be generated at multiple frequencies simultaneously using the same groove and incoupling angle, thus enabling operation of the plasmonic interferometer event at frequencies far from the metal resonance, and extraction of the analyte dispersion relation in a broad wavelength range. Hence, plasmonic interferometers offer a novel scheme for SPP excitation and refractive index detection using SPP interference, retaining real-time and label-free sensing capabilities of existing technologies.

Figure 2:
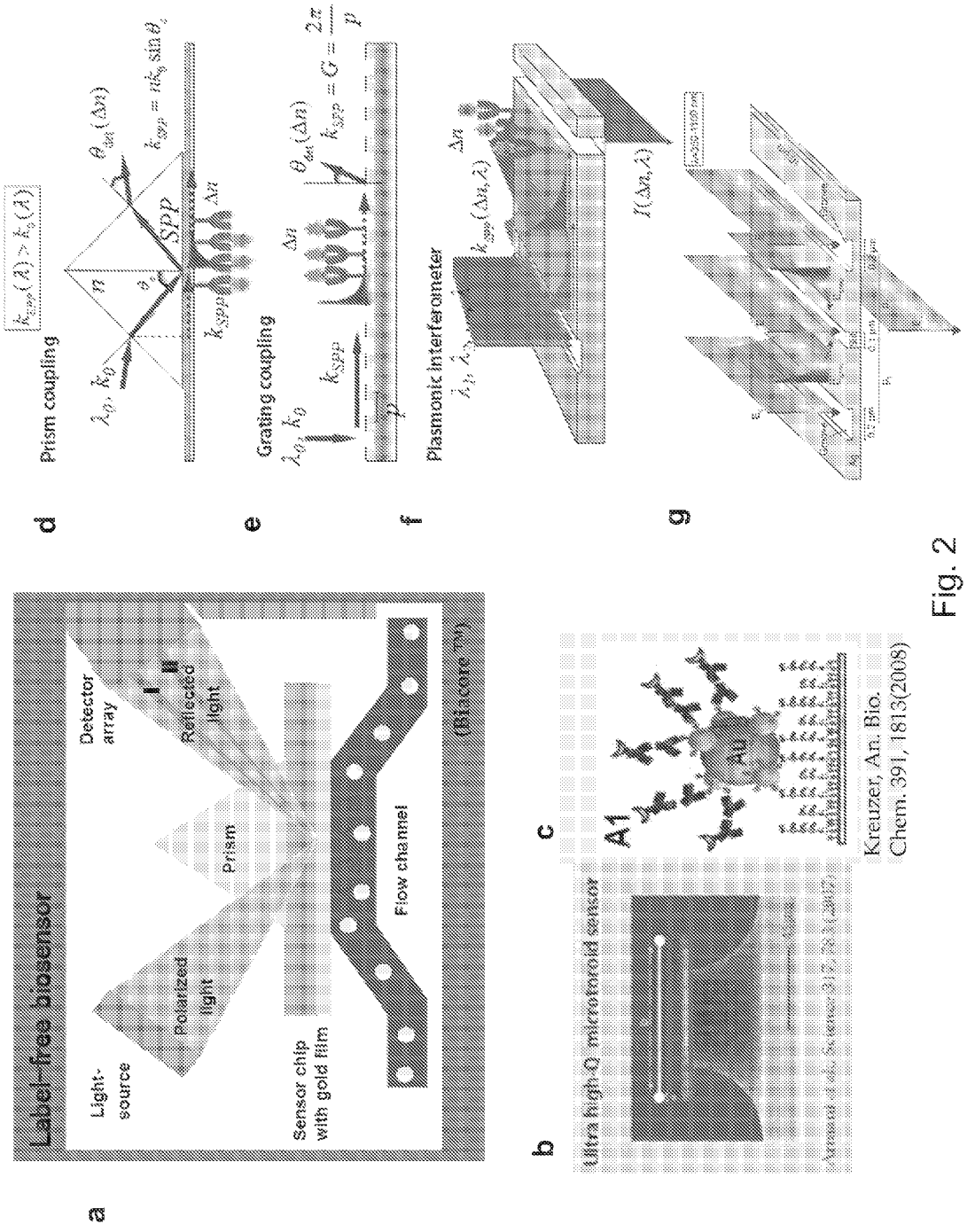
Figure 3:
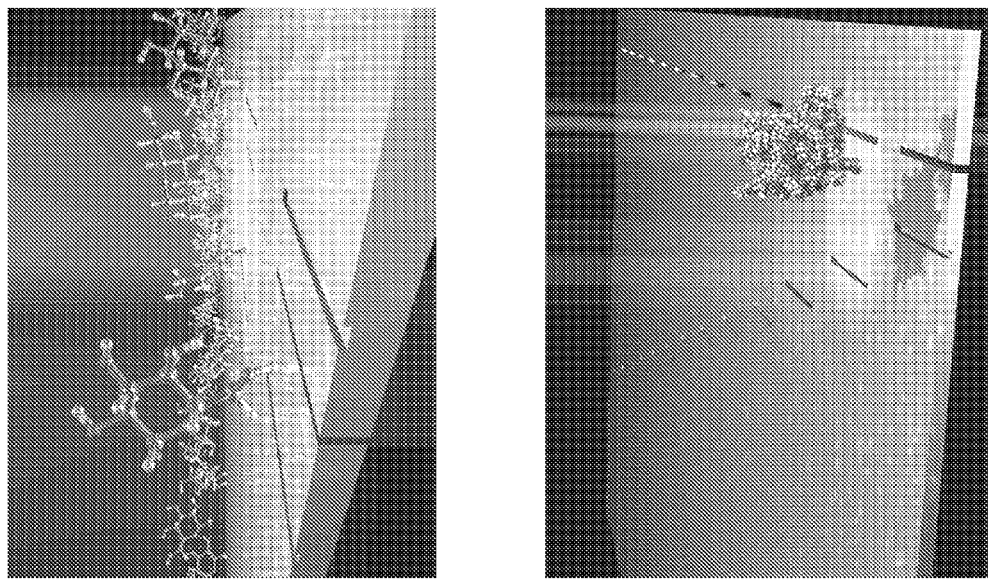
FIG. 3 shows schematics of the general applications of the plasmonic interferometer including: (a) an in-situ spectroscopic ellipsometer for measuring the dispersion relation and optical constants of dielectric materials at the metal surface, (b) a plasmonic interferometer for small molecule detection (e.g. glucose, drugs) (c) a plasmonic interferometer coupled with oxidative and chromogenic dyes for enhanced sensing, and (d) a plasmonic interferometer for protein (e.g. cytokines) sensing.
Figure 3:
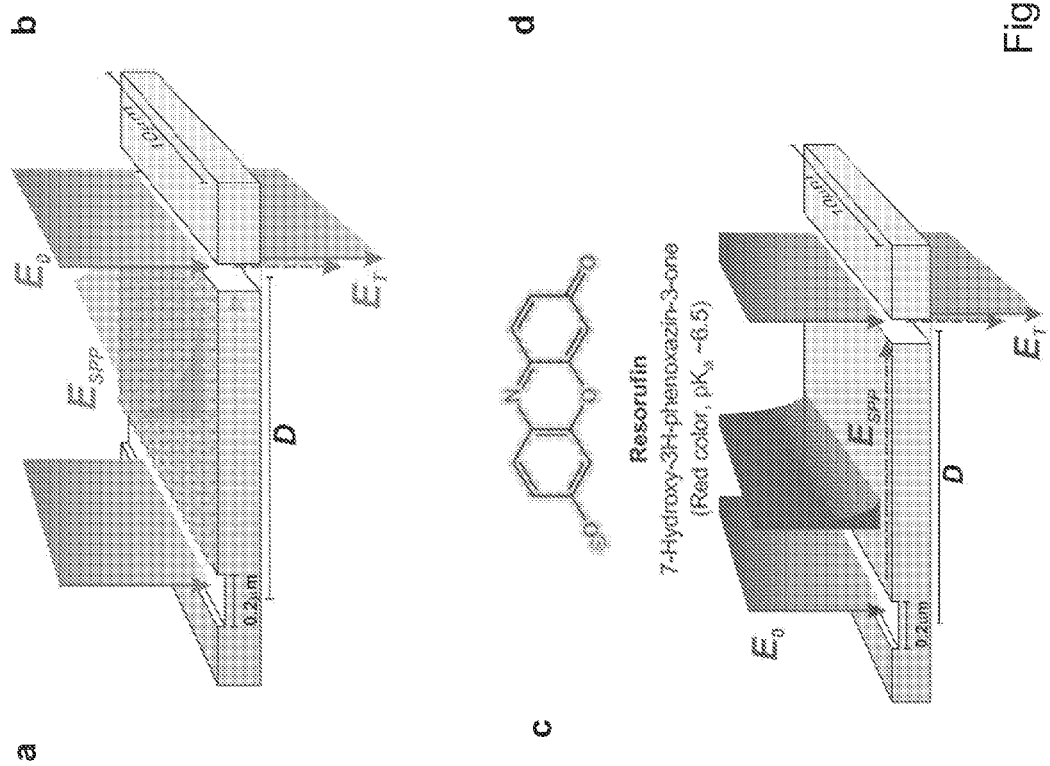

An exemplary plasmonic interferometer is shown in FIG. 2g. The device includes two grooves located on opposite sides of an aperture, shown here as a slit. The first and second grooves are spaced apart from the slit by distances $p_1$ and $p_2$, respectively. FIG. 2g schematically shows that the plasmonic interferometer works by optical interference between the two counter-propagating SPP waves ($E_{spp1}$, $E_{ssp2}$) and the incident beam at the slit location ($E_0$). Light incident upon the left-side groove generates SPPs propagating toward the slit. At the slit location, and for each frequency, the SPP (with amplitude $E_{SPP1}$) will interfere with the coherent incident beam ($E_0$). Light incident on the right groove also excites an SPP with amplitude $E_{SPP2}$, traveling along the metal surface and interfering with the incident beam and the other SPP wave at the slit location. The light that is transmitted through the slit is characteristic of the SPP waves and the dielectric medium through which the SPP waves propagate. FIG. 2f is a schematic illustration of the device (only a single groove is shown for simplicity), in which the surface has been modified to provide a surface chemistry (indicated by tethered 'horseshoe' 100) capable of binding the target analyte (indicated as 'starburst' 110).

Fabrication and Modeling the Optical Response of the Plasmonic Interferometers.

Figure 4:
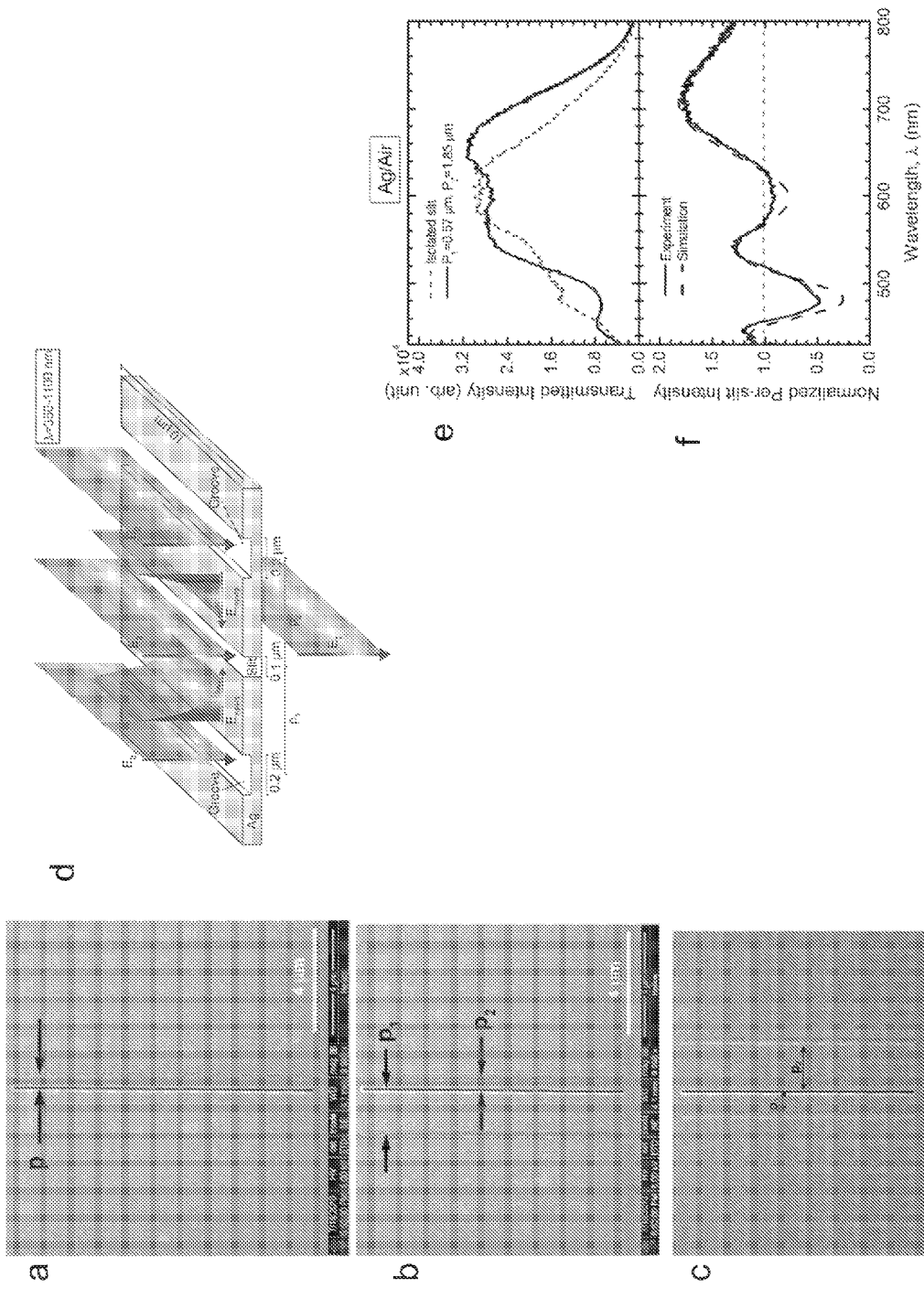

According to alternative aspects of the present disclosure, plasmonic interferometers were fabricated by focused ion beam milling on a 300 nm-thick Ag film, previously evaporated on a clean glass slide. Different kinds of plasmonic interferometers were designed and fabricated, consisting, for example, of a groove-slit pair with separation distance p, and a novel groove-slit-groove design, with slit-groove separation distances (i.e. interferometer arms) p1 and p2, varying in the range 250 nm-2 µm, in steps of 25 nm. Moreover, several individual slits were etched on the same film to serve as a reference. FIGS. 4a-c show SEM micrographs of representative devices. The grooves and slits were 200 nm and 100 nm wide, 50 nm and 300 nm deep, respectively, and 10 µm long. In FIG. 4a, the separation distance between the groove and the slit is p=250 nm, while in FIG. 4b, the slit-groove separation distances are $p_1$=1670 nm and $p_2$=250 nm. FIG. 4c shows another groove-slit-groove interferometers with different slit-groove separation distances. The dimensions of the slit and groove affect the performance and sensitivity of the interferometer. The dimensions can vary, for example, to excite particular wavelengths or to adjust the launching phase of the surface plasmons. The length of the slit and grooves can vary. The length can range, for example, between 500 nm and 100 µm. The width of the slit and grooves can also vary. The width can vary between 50 nm and 500 nm. The depth of the grooves can also vary. The depth can range, for example, between 5 nm and 300 nm.

FIG. 4d shows another schematic an interferometer according to aspects of the present disclosure. Light incident upon the left-side groove generates a collective oscillation of the conduction electrons in the metal film that can propagate toward the slit, in the form of a surface wave, along the metal/dielectric interface. This SPP wave has a complex amplitude ($E_{SPP1}$), whose phase and amplitude can be affected by any chemical analyte encountered along the optical path. Light incident on the right groove goes through the same process and has an amplitude, $E_{SSP2}$. Useful information about the kind and quantity of analytes adsorbed on the surface can be retrieved by interfering the surface wave with the incident beam ($E_0$) at the slit location, which causes a change in the total light field transmitted at the output mouth of the slit ($E_T$). As a result of the interference process between the surface plasmon and the incident light beam, the light intensity transmitted through the slit can be modulated, i.e. either enhanced or suppressed, depending on whether a constructive or destructive interference occurs. By measuring the light intensity transmitted through the slit as a function of wavelength and monitoring the change thereof caused by the presence of an analyte, we can estimate the amount and fingerprints of the adsorbed chemical species.

FIG. 4e shows the representative spectra for light intensity transmitted through an isolated nano-slit and through the nano-slit of a groove-slit-groove interferometer, with arms $p_1$=0.57 µm and $p_2$=1.85 µm, respectively. A halogen light source was aligned to the optical axis of a Nikon Ti Eclipse inverted microscope. The beam was collimated at normal incident onto the sample surface with respect to the silver/air interface. The light intensity transmitted through the slit of the device was collected by an objective lens and sent to a single grating monochromator, then detected with a digital CCD array. In order to detect the modulation effects caused by the interference between the surface plasmons and the incident beam, the transmission spectrum was normalized by dividing the light intensity transmitted through the groove-slit-groove interferometer by the transmission spectrum of an isolated slit. The resulting normalized per-slit transmitted intensity spectrum is reported in FIG. 4f. Compared to an isolated slit, light intensity can be enhanced or suppressed because of constructive or destructive interference. The observed intensity modulation in the normalized transmission spectrum for a GSG device results from interference (at the slit location) between the two counter-propagating SPPs originating from in-plane diffractive scattering of light at the two grooves, and the incident beam. The slit in between the two grooves effectively acts as a "spatial mixer" of the three field amplitudes (incidence beam plus the two SPP waves generated by diffractive scattering). The light intensity transmitted through the slit contains information of the relative phase difference and amplitude of the different beams. FIG. 4f also reports the simulated normalized per-slit transmission through the slit of the GSG plasmonic interferometer (dashed line) using the model developed above. The agreement between the experimental and simulated normalized per-slit transmission spectra, demonstrates that transmission maxima and minima result from constructive and destructive interference between the incident beam and the two counter-propagating SPPs excited by diffractive scattering at each groove position. SPPs can therefore be generated at multiple wavelengths using the same incident angle, a novel capability not possible in SPR techniques based on prism- and grating-coupling.

A total of 568 devices over an area of 3.5×4.0 mm² were etched using an automated scripting routine implemented to control the focused ion beam parameters and stage position during milling. This corresponds to a density of >4,000 devices per centimeter squared. The device density range can be as low as one single interferometer per chip, or as high as one million (or greater) per millimeter squared. After fabrication, light transmitted intensity through each device was measured using broadband illumination at normal incidence, and a monochromator to disperse the transmitted intensity onto a CCD camera to detect a real-time transmission spectrum.

Figure 5:
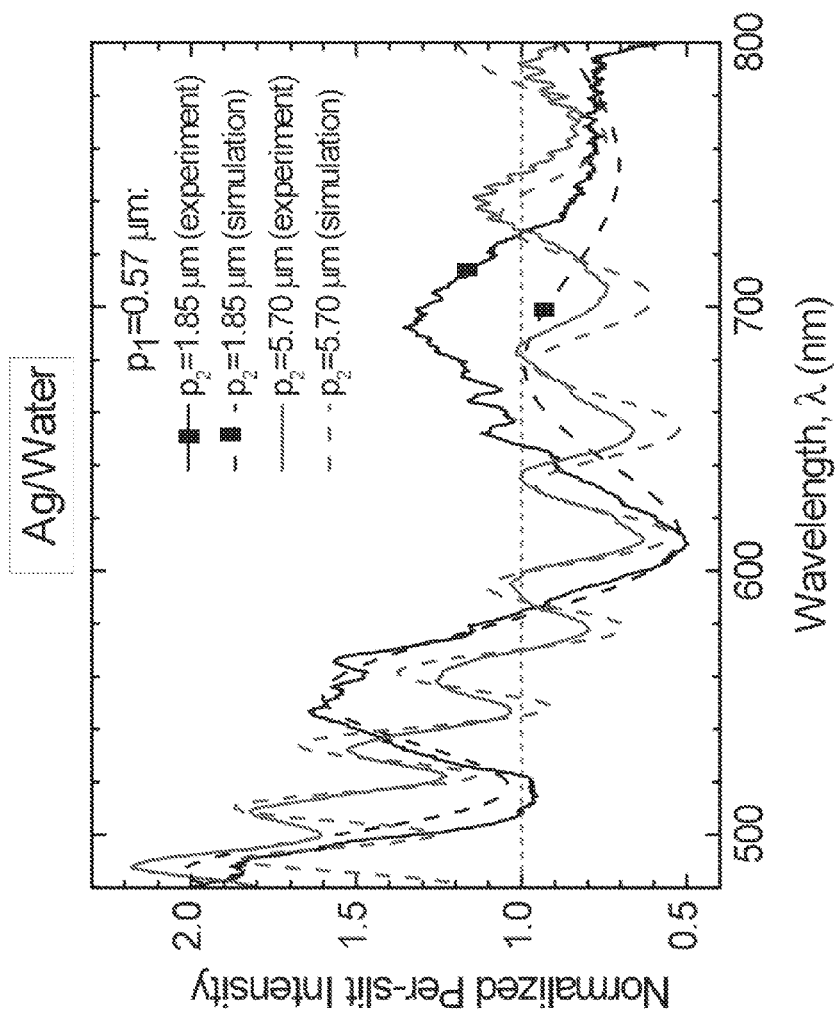
FIG. 5 shows normalized per-slit transmitted intensity spectra (experimental and simulated) for two GSG plasmonic interferometers, according to aspects of the present disclosure.

FIG. 5 shows the experimental (solid lines) and simulated (dashed lines) normalized transmitted intensity spectra for two plasmonic interferometers with constant $p_1$=0.57 µm and different $p_2$ lengths: 1.85 µm (black lines) and 5.70 µm (red lines). From this figure, a greater number of intensity maxima and minima can be observed by increasing $p_2$, resulting in more wavelengths at which constructive and destructive interference occurs. These results suggest that the device sensitivity can be improved at various wavelengths by simply increasing the groove-slit separation distance. This distance is only limited by the ohmic and scattering losses of SPPs, which in general reduce the SPP propagation length, and by the spatial and temporal degree of coherence between the SPPs and the incident beam, needed to determine the interference effect.

An SPP interference model was developed to predict the optical response for the plasmonic interferometer, extending reported models dealing with groove diffraction and SPP interference. As shown in FIG. 4d, light incident upon the left-side groove generates SPPs propagating toward the slit. At the slit location, and for each frequency, the SPP (with complex amplitude $E_{SPP1}$) will interfere with the coherent incident beam ($E_0$). Light incident on the right groove also excites an SPP with amplitude $E_{SPP2}$, traveling along the metal surface and interfering with the incident beam and the other SPP wave at the slit location. Though the slit can also generate SPPs, these are mainly scattered back in free space by out-of-plane scattering once they reach the neighboring grooves. Therefore, slit-generated SPPs do not contribute significantly to the transmitted intensity through the same slit. Accordingly, for this model, only the SPPs originating from the two grooves will be considered. This assumption is verified by the excellent agreement between simulated and experimental results.

The resulting total transmitted intensity through the slit of a GSG two-arm plasmonic interferometer is given by $$I_T = |E_T|^2 = I_S |1 + \beta_1 e^{i\phi_1} + \beta_2 e^{i\phi_2}|^2$$

where $I_S$ is the light intensity transmitted through an isolated slit with identical width and length, subscripts 1 and 2 denote the SPP contributions originating from the left and right groove, respectively, $\beta_{1,2}$ accounts for the effective efficiency of SPP excitation via diffractive scattering by each groove, and $\phi_{1,2}$ is the total phase shift of the SPP including a complex phase accounting for propagation and absorption in the metal and dielectric material, and a scattering phase accrued by the SPP upon excitation by each groove, given by $$\varphi_{1,2} = \frac{2\pi}{\lambda} p_{1,2}(n_{SPP} \mp n_d \sin\theta) + \varphi_{G1,2}$$

where $\lambda$ is the free-space wavelength of the incident beam, $p_{1,2}$ is the groove-slit distance, $\theta$ is the angle between the incident light beam and the normal to the sample surface ($\theta$=0 herein), $n_{SPP}$ is the complex refractive index of the SPP given by $n_{SPP}=[\in_m \in_d/(\in_m+\in_d)]$ where $\in_m$ is the complex dielectric constant of the metal, $\in_d$ is the complex dielectric constant of the material above the metal, $n_d$ is the refractive index of the dielectric material, and $\phi_{G1,2}$ is an additional phase shift due to the initial scattering by the groove. The SPP propagative phase is affected by several tunable parameters, such as the incident wavelength ($\lambda$), the distance between the slit and the grooves ($p_{1,2}$), and the refractive index of the dielectric material, $n_d = \in_d^{1/2}$.

If the two grooves are identical and the dielectric material on top of each is the same, then the SPP excitation efficiencies and scattering phases at each groove are the same, i.e., $\beta_1 = \beta_2 = \beta$ and $\phi_{G1} = \phi_{G2} = \phi_G$. The transmitted intensity through the slit (normalized to the light intensity transmitted through an isolated slit) then becomes $$I_T/I_S = |1 + \beta\{e^{i[p_1(k_{SPP}-k\sin\theta)+\phi_G]} + e^{i[p_2(k_{SPP}+k\sin\theta)+\phi_G]}\}|^2$$

where $k_{SPP}=2\pi n_{SPP}/\lambda$ and $k=2\pi n_d/\lambda$. As a result of the interference process between the SPP waves and the incident beam, the light intensity transmitted through the slit can be either enhanced or suppressed, depending on whether constructive or destructive interference occurs. In comparison, light transmitted through the slit of a plasmonic interferometer consisting of only one groove-slit pair will be the result of a two-beam interference (SPPs from the two grooves plus the incident beam), which would result in reduced beatings and constructive/destructive interference effects. The GSG plasmonic interferometers clearly show better sensitivity compared to GS devices and were chosen accordingly for the sensing experiments. To verify the model, the plasmonic interferometers were illuminated using a collimated, broadband light source normally incident upon the sample surface, with a power density of ~10⁻² W/cm². A 40× objective lens was used to collect the far-field light intensity transmitted through the slit of each plasmonic interferometer, then dispersed using a single-grating spectrograph and detected by a CCD camera. Spectral resolution of the optical setup was ~0.4 nm; the number of counts and acquired spectra per experiment were adjusted to ensure a statistical error of <0.1% in the measured transmitted intensity.

Figure 6:
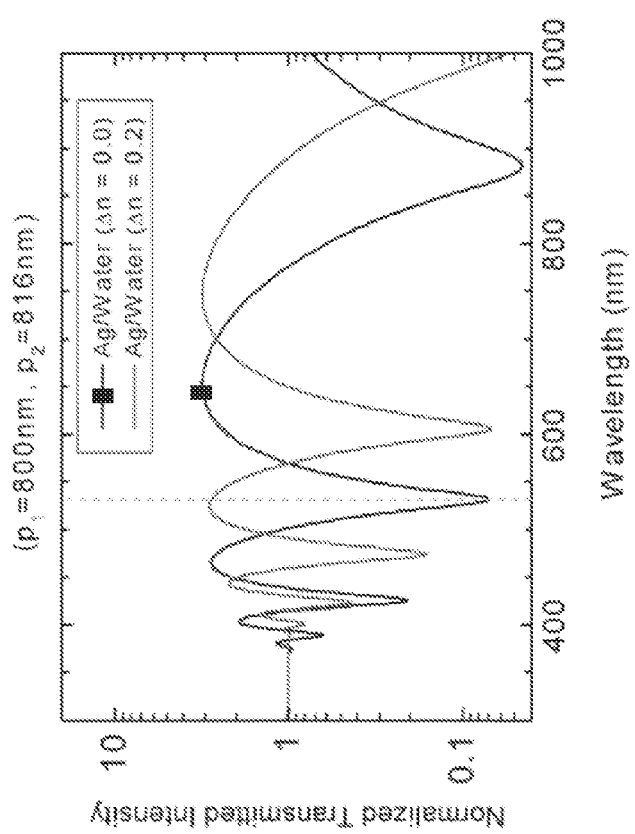
FIG. 6 shows predicted normalized light transmission, as a function of incident wavelength, through a slit aperture in a plasmonic interferometer immersed in water, according to aspects of the present disclosure.

FIG. 6 shows a proposed extension of the model to calculate the normalized transmitted intensity for a groove-slit-groove interferometer immersed in water. Specifically, FIG. 6 shows the predicted normalized light transmission through a slit aperture in a groove-slit-groove interferometer, with $p_1$=800 nm and $p_2$=816 nm, as a function of incident wavelength. The black curve has been calculated by using the dispersive dielectric constant of de-ionized water and the optical constants of Ag. Upon introduction of small quantities of analyte in water corresponding to a refractive index change $\Delta$n=0.2, a clear modification of the transmission curve occurs. In particular, it is possible to notice that the light intensity at 532 nm goes from a minimum to a maximum upon introduction of the analyte in water. The relative change of intensity before and after index change is ~40.

Figure 7:
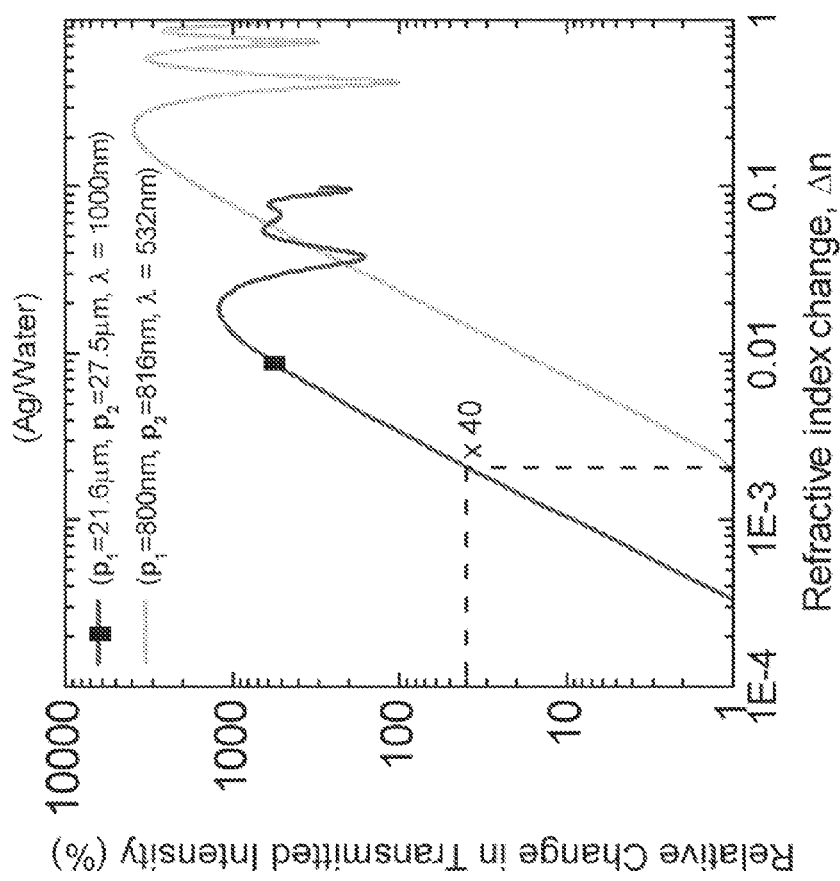
FIG. 7 shows predicted relative percent change in light intensity transmitted through the slit of two plasmonic GSG interferometers, as a function of refractive index change induced by the presence of cytokines.

FIG. 7 shows the predicted relative percent change in light intensity transmitted through the slit of two plasmonic groove-slit-groove interferometers, as a function of refractive index change induced by the presence of cytokines Specifically, the gray line in FIG. 7 reports a more systematic study of the percent change in transmitted light intensity, defined as $[I_T(\Delta n)-I_T(0)]/I_T(0)$, recorded at 532 nm for the same device as a function of refractive index change. It is worth noting that in going from $\Delta n=0.002$ to $\Delta n=0.2$, the interferometer response varies from 1% to 4,000% relative change in light transmitted intensity, which corresponds to a relative gain of $2\times10^4$ per refractive index unit. The sensitivity can be further enhanced by using longer wavelengths and longer slit-groove separation distances. The square-identified line in FIG. 7 reports the relative change in light transmitted intensity for a device with $p_1=21.6$ μm and $p_2=27.5$ μm at a wavelength $\lambda=1000$ nm.

For a refractive index change of $2\times10^{-3}$ the interferometer with longer arms has a 40 times higher signal response, with a gain of $7\times10^4$. Further analysis of the interferograms generated by a properly functionalized optical biosensor can determine the presence of cytokines and can generate a calibration curve (similar to the one reported in FIG. 7) as a function of cytokine concentration (in the range of 1-100 nM, corresponding to an estimated refractive index change of $\Delta n=3\times10^{-4}-3\times10^{-2}$) with extremely high sensitivity and in real time.

Figure 8:
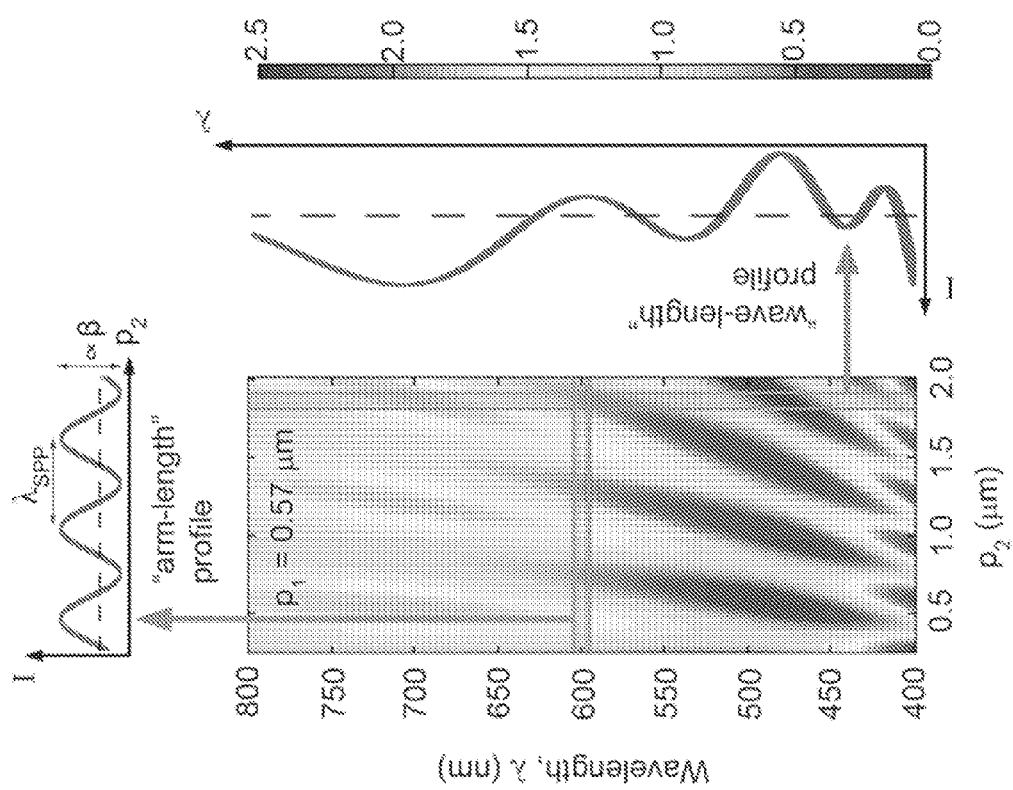
FIG. 8 shows a simulated 2D color map of normalized light intensity transmitted through the slit of several plasmonic interferometers with $p_1$=0.57 µm, as a function of groove-slit arm length $p_2$ (horizontal axis) and wavelength λ (vertical axis). Typical normalized transmitted intensity plots obtained by horizontal or vertical cuts across the color map (indicated by gray boxes) are also shown.

FIG. 8 shows a simulated color map of normalized per-slit light intensity transmitted through the slit of a series of plasmonic interferometers in air, at a given $p_1=0.57$ μm and varying $p_2=0.25$-2.0 μm, as a function of wavelength (400-800 nm). To construct this color map, normalized transmission spectra or "wavelength profiles" (vertical gray box in FIG. 8) for plasmonic interferometers with varying $p_1$ and $p_2$ were stacked according to increasing $p_2$. The color of each pixel in the maps represents the measured normalized transmitted intensity $I_T$ for a specific combination of slit-groove separation distances and wavelength, i.e. we are plotting $I_T(p_1, p_2, \lambda)$. The color bar shows that light transmission through a slit flanked by the two grooves can be enhanced by as much as a factor 2.5 compared to an isolated slit, and suppressed by the same amount. From this map, a horizontal "cut" (for example at 600 nm, as indicated by the horizontal gray box in FIG. 8) can reveal an intensity profile as a function of arm length $p_2$, for a given incident wavelength. According to equations mentioned above, the difference between intensity maxima and minima can be shown to be proportional to the SPP excitation efficiency from the groove. Therefore, such horizontal cuts in the experimental color maps are useful in determining the SPP excitation efficiency at various wavelengths.

Figure 9:
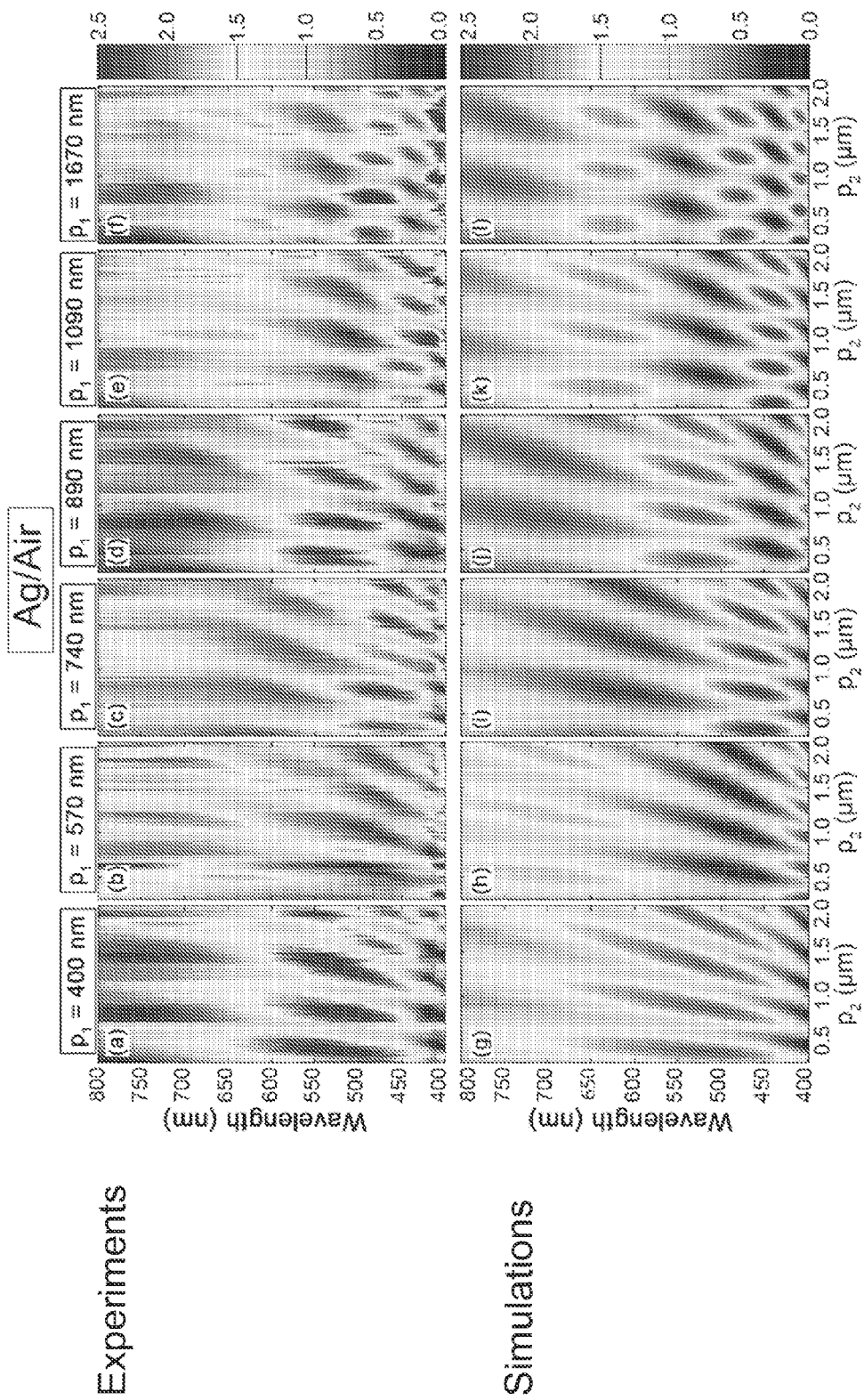
FIG. 9a-l shows color maps of experimental and simulated normalized light transmission spectra collected through plasmonic interferometers at different combinations of $p_1$ and $p_2$ according to aspects of the present disclosure.

FIG. 9 shows a comparison between experimental results and simulation results for normalized light transmission spectra through the slit of hundreds of plasmonic interferometers consisting of a slit aperture flanked by two grooves located at different slit-groove separation distances. Each of the six panels reports color maps of transmission spectra through devices with varying slit-groove separation distances ($p_1, p_2$) normalized by the spectrum of an isolated reference slit. In order to understand the interference phenomenon, we have to realize that each groove acts as a localized, efficient source of surface plasmon polaritons (SPPs) traveling toward the neighboring slit. At the slit location, the two propagating SPPs interfere with the incident light beam at the slit location, thus causing either constructive or destructive interference. Under aspects of the present disclosure, an analytical model can describe the interference process. The resulting color maps are presented in the bottom panel of FIG. 9. These color maps show remarkably good agreement with the experimentally determined data. In particular, focusing the attention on one of the six maps (e.g., the first map from the right corresponding to $p_1=1670$ nm) it is possible to appreciate the excellent correspondence between the peaks of maximum intensity enhancement predicted by the proposed interference model and the experimentally measured peak positions.

The excellent agreement between experiment and simulation strongly supports the SPP interference model, thus providing for full control and tunability of the light transmission as a function of any of the three parameters: $p_1$, $p_2$ and $\lambda$. In addition, a fit of the experimental data using the SPP interference model allows the determination of the effective SPP excitation efficiency ($\beta$) as a function of wavelength. Specifically, $\beta$ decreases from ~0.3 at 460 nm to ~0.15 at 760 nm. Accordingly, color maps of transmitted intensity normalized to single slit for Ag/Air and Ag/water interfaces were simulated, using the well-known dielectric constant for silver and water.

Application of Plasmonic Interferometry to Sensing of Dielectric Materials.

According to aspects of the present disclosure, methods of fabrication and testing of nanohole, nanoslit, and nanogroove arrays that enable resonant enhancements of the incident laser intensities over a broad spectral range are provided. The same nano-patterned structures can be used to achieve the following simultaneously: (a) resonantly enhance the intensity of the incident light source used to excite the propagating surface plasmons and (b) enhance the device sensitivity to small refractive index change (measured in terms of relative change in transmitted intensity).

Figure 10:
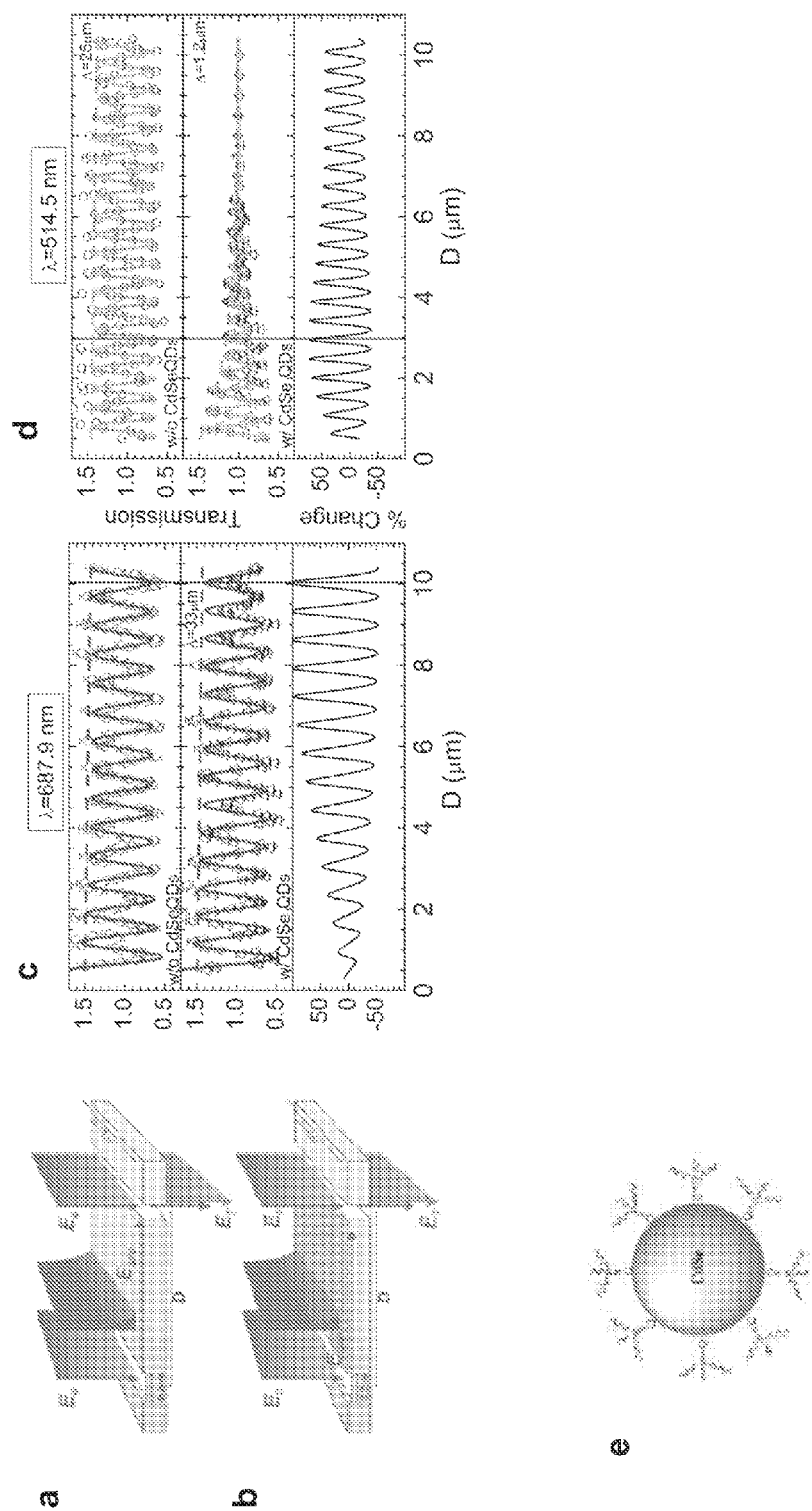
FIG. 10 shows schematics of (a) uncoated and (b) CdSe coated plasmonic interferometers, (c-d) charts of measured transmitted intensities with and without coating at 687.9 nm and 514.5 nm, respectively, and (e) a schematic of a CdSe quantum dot used to coat the plasmonic interferometer surface.

The sensitivity of the interferometer to surface changes (such as would be the case when an analyte is present) is demonstrated by modification of the surface using various analytes deposited on the sensor surface, such as semiconductor (CdSe) quantum dots (QDs), glucose molecules in solution, fluorescent dyes in solution, or small proteins in solution. FIG. 10a shows a schematic of uncoated interferometer consisting of a groove and a slit milled in a metal film; upon uniform illumination of the device with a focused Gaussian laser beam, the intensity measured through the slit aperture results from the interference between the propagating SPP and the incident light. As a function of separation distance D, the light intensity transmitted through the slit of different interferometers shows maxima and minima, corresponding to constructive and destructive interference between the SPP and the incident light beam. FIG. 10c shows experimental measurements of the light intensity at 687.9 nm transmitted through the slit of several uncoated interferometers. Each data point corresponds to the transmission intensity through an interferometer with specific slit-groove separation distance, normalized by the light intensity transmitted through an identical but isolated slit aperture on the same film. The ensemble of data is hereafter referred to as the sensor "interferogram." The top panel of FIG. 10c shows the transmitted intensities for uncoated interferometers (in air), which serve as our reference interferogram. When coated with a uniform, 20 nm-thick film of semiconductor (CdSe) quantum dots (QDs), as schematically shown in FIG. 10b, the sensor array shows a remarkably different interferogram (See middle panel of FIG. 10c). The interferogram peaks and valleys shift toward lower values of D, as a result of the enhanced refractive index. For a 10-μm long interferometer, introduction of the QDs causes a transmission minimum to become a transmission maximum, as indicated by the vertical blue line. The bottom panel of FIG. 10c reports the measured change in light transmission through coated interferometers, relative to uncoated interferometers, as a function of groove-slit separation distance. This relative change can be as much as 100% for a 10 μm-long interferometer.

The results suggest a detection capability as low as 0.6 ng/mm$^2$ in analyte surface mass density, corresponding to 0.1% change in refractive index for this particular design. The disclosed approach enables measurement not only of the real part of the refractive index, but of the imaginary part as well, which is related to the absorption properties of the analyte to be detected. FIG. 10d shows the experimental interferograms for uncoated (top panel) and QD-coated (middle panel) interferometers recorded at 514.5 nm. At this wavelength, the SPP energy is greater than the bandgap of the CdSe QDs (designed to have an absorption edge at 600 nm). The SPP can therefore be absorbed while propagating along the metal/dielectric interface (See schematic in FIG. 10b), causing an exponential decrease of the transmitted intensity as a function of separation distance D, in addition to a phase shift. The presence of the CdSe QDs is revealed as a change in both phase and envelope amplitude of the sensor interferogram. FIG. 10e is a schematic of the CdSe quantum dot used to coat the surface in this series of experiments. It includes a CdSe core and a trialkyl phosphate surface functionalization.

The light intensity transmitted through the slit of each interferometer can be thought of as the result of an interference process between the incident beam (with amplitude $E_0$) and the propagating surface plasmon polariton (with amplitude $E_{SPP}$), whereas more than one SPP can be excited using more than one groove as the excitation source. The phase difference between the propagating surface plasmon polariton and the incident beam leads to a modulated light intensity whose expression is given below. The phase difference $\delta$ carries information of the analyte through the refractive index $n_{SPP}$.

$$E_T = TE_0 + T\beta e^{i\delta} E_0$$

$$I_T = |ET|^2$$

$$= I_0 |1 + \beta e^{i\delta}|^2$$

$$\delta = k_{SPP} D + \varphi_g + i\frac{\alpha}{2} D$$

$$\boxed{\frac{I_T}{I_0} = 1 + \beta^2 e^{-\alpha D} + 2\beta e^{-\alpha D/2} \cos[n_{SPP} kD + \varphi_g]}$$

Figure 11:
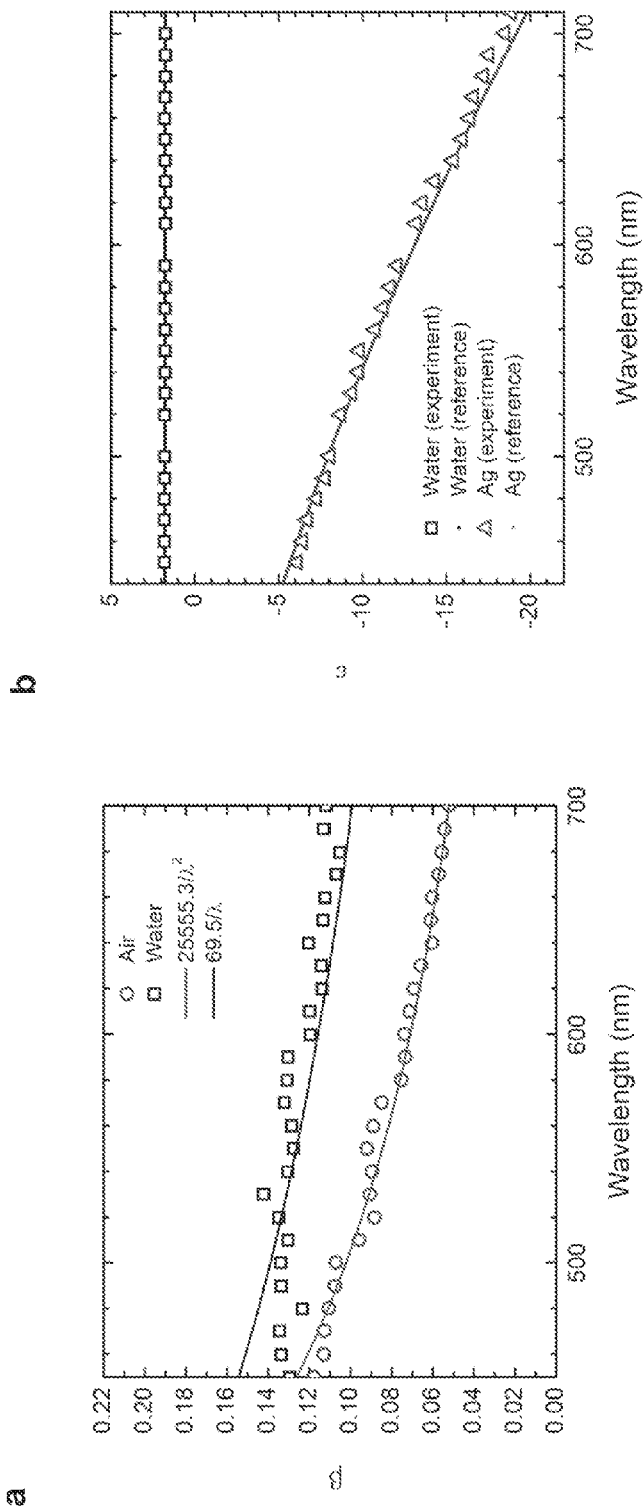
FIG. 11 shows (a) the effective SPP excitation efficiency in Ag/air and Ag/water interfaces as a function of wavelength; (b) the extracted dielectric constant of Ag and water as a function of wavelength.

So with the normalized transmitted intensity v. groove-slit separation distance D at a certain wavelength, effective SPP excitation efficiency $\beta$ and SPP refractive index can be extracted by data analysis. FIG. 11a shows $\beta$ as a function of wavelength in Ag/air and Ag/water interface. In addition, the refractive index of either metal or dielectric material can be extracted if the other constant is known. FIG. 11b shows the dispersions of water and Ag, which agree well with the data from references. Accordingly, the dispersion of any dielectric above the sensing surface, i.e. the dielectric's fingerprint, can be found through data manipulation, which makes a spectroscopic ellipsometer. And it is also feasible to find out the composition of the dielectric material on the surface.

Application of Plasmonic Interferometry to Glucose Sensing.

Glucose is an ideal analyte for sensing applications because (1) it was one of the first molecules for which a biosensor was developed; (2) 346 million people worldwide are affected by diabetes and thus, require constant monitoring of their glucose levels; and (3) a good number of papers report results on glucose sensing, which can serve as a basis for comparing the performance of our plasmonic interferometers and determining the feasibility for cytokine and other biochemical analyte detection. Moreover, it would be ideal to find alternative methods able to sense even lower glucose concentrations, potentially allowing the use of saliva or tears for noninvasive glucose sensing and real-time monitoring. It should be noted that the principles described herein can be applied to monitor the concentration of any organic or non-organic analyte. To illustrate the feasibility for glucose sensing, thousands of plasmonic interferometers were patterned onto a single biochip equipped with a polydimethylsiloxane (PDMS) micro-channel. Various concentration of glucose solutions in water were flowed into and out of the microfluidic channel at a constant rate of 150 μL/min using two microsyringe pumps, and the transmitted light intensity was monitored for each plasmonic interferometer. The continuous flow together with the extremely low power density allowed the temperature of the device to be held constant throughout the sensing experiment. The microfluidic system can be part of a sample holder system. According to aspects of the disclosure, the sample holder can further include inlet and outlets positioned to permit inflow and outflow of a second fluid in the sample holder.

A compact, high-throughput plasmonic sensor based on surface plasmon interferometry optimized for real-time monitoring of glucose in aqueous solutions consists of a spatially dense, planar array of plasmonic interferometers (>1,000/mm$^2$), where each interferometer is composed of 100 nm-wide, 10 μm-long grooves flanking a 200 nm-wide slit etched in a 300 nm-thick silver film using focused ion-beam milling. The distances between each groove and the slit were varied between 0.25 to 10 μm in steps of 25 nm. The detection limit of the plasmonic sensor for glucose in aqueous solutions is 5.5 μM with a sensitivity of 105,000%/RIU (refractive index units) at 590 nm. Based on results shown in FIG. 5, the device with $p_1$=0.57 μm and $p_2$=5.70 μm was chosen to perform the glucose sensing experiment. As discussed above, FIG. 12a illustrates the normalized per-slit transmitted intensity spectra of this device, measured as a function of wavelength for increasing concentrations of an aqueous glucose solution. A wavelength shift ($\Delta\lambda$) is observed at all incident wavelengths. Increasing glucose concentration enhances the refractive index of water (the dielectric material), and results in a red-shifted interference spectrum.

Figure 12:
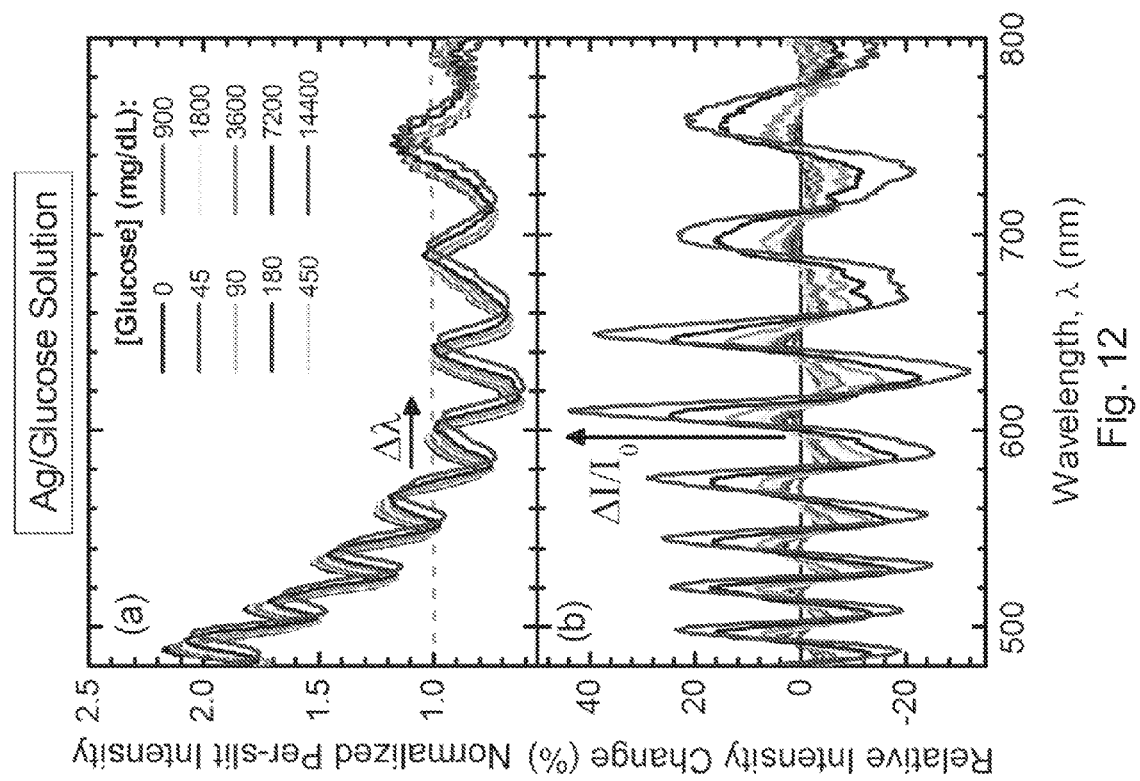
FIG. 12 shows (a) normalized per-slit transmitted intensity spectra of a GSG device measured at various concentrations of glucose in water; and (b) relative intensity change spectra normalized to pure water at various concentrations of glucose in water.

FIG. 12(a) shows the normalized per-slit transmission spectra of a groove-slit-groove plasmonic interferometer with $p_1$=0.57 μm and $p_2$=5.70 μm, measured at various concentrations of glucose in water. A wavelength shift ($\Delta\lambda$) is observed at all wavelengths. Increasing glucose concentration enhances the refractive index on the surface, thus resulting in the observed red-shift in the normalized transmission spectra.

In contrast to existing approaches that use single excitation wavelength, the proposed device operates in a broad wavelength range, allowing a polychromatic detection of chemical analytes. By correlating the wavelength shift with the known concentration, a calibration curve can be determined for each device.

FIG. 12(b) shows another figure of merit used to characterize our device response, i.e. the relative intensity change ($\Delta I/I_0$) normalized to pure water for the same device, at various concentrations of glucose in water. Some wavelengths do not show any significant change in transmitted light intensity, forming "nodes" that are characteristic of each specific device. For this particular device, the maximum relative intensity change is achieved at a wavelength of 610 nm, with values of up to 40%. In summary, by monitoring the $\Delta\lambda$ and $\Delta I/I_0$ at all wavelengths and for various glucose concentrations, we were able to sense glucose concentrations in a broad range from 0.1-20,000 mg/dL corresponding to a change in refractive index units (RIU) of ~0.014.

The relative intensity change ($\Delta I/I_0$) is given by $$\frac{\Delta I}{I_0} = \frac{I_{glucose} - I_{water}}{I_{water}} \times 100\%$$

where $I_{glucose}$ is the transmitted light intensity through the slit of a plasmonic interferometer at a specific glucose concentration, and $I_0 = I_{water}$ is the reference transmitted intensity through the slit of the same interferometer in pure water (i.e., zero glucose concentration).

Figure 13:
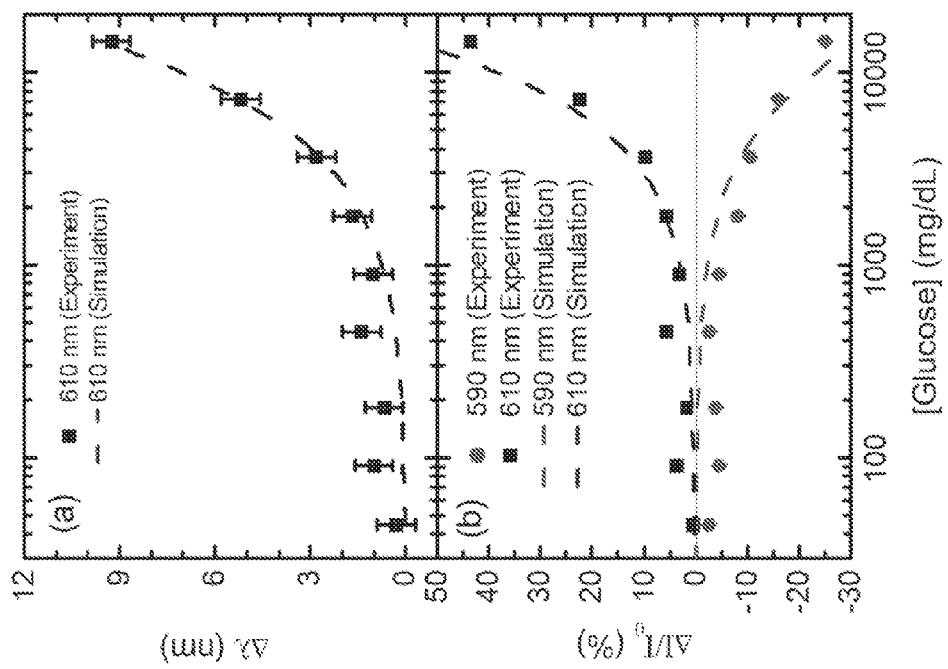
FIG. 13a-b shows calibration curves for a plasmonic interferometers.

FIG. 13 shows the performance of the same device analyzed by plotting the experimental and simulated values for $\Delta\lambda$ and $\Delta I/I_0$ as a function of glucose concentration. The experimental (symbols) and simulated (dash line) $\Delta\lambda$ at a center wavelength of 610 nm and $\Delta I/I_0$ at 590 nm (gray line and circles) and at 610 nm (black line and squares) are shown in FIG. 13, panels a and b, respectively. The simulated curves are in excellent agreement with the experimental data. $\Delta\lambda$ and $\Delta I/I_0$ show significant variation as a function of glucose concentration, and can therefore be used to infer the concentration of glucose in solution. Furthermore, as shown in FIG. 13(b), it is evident that at close but different wavelengths, the device response can be remarkably different, with higher sensitivity observed at 610 nm.

Figure 14:
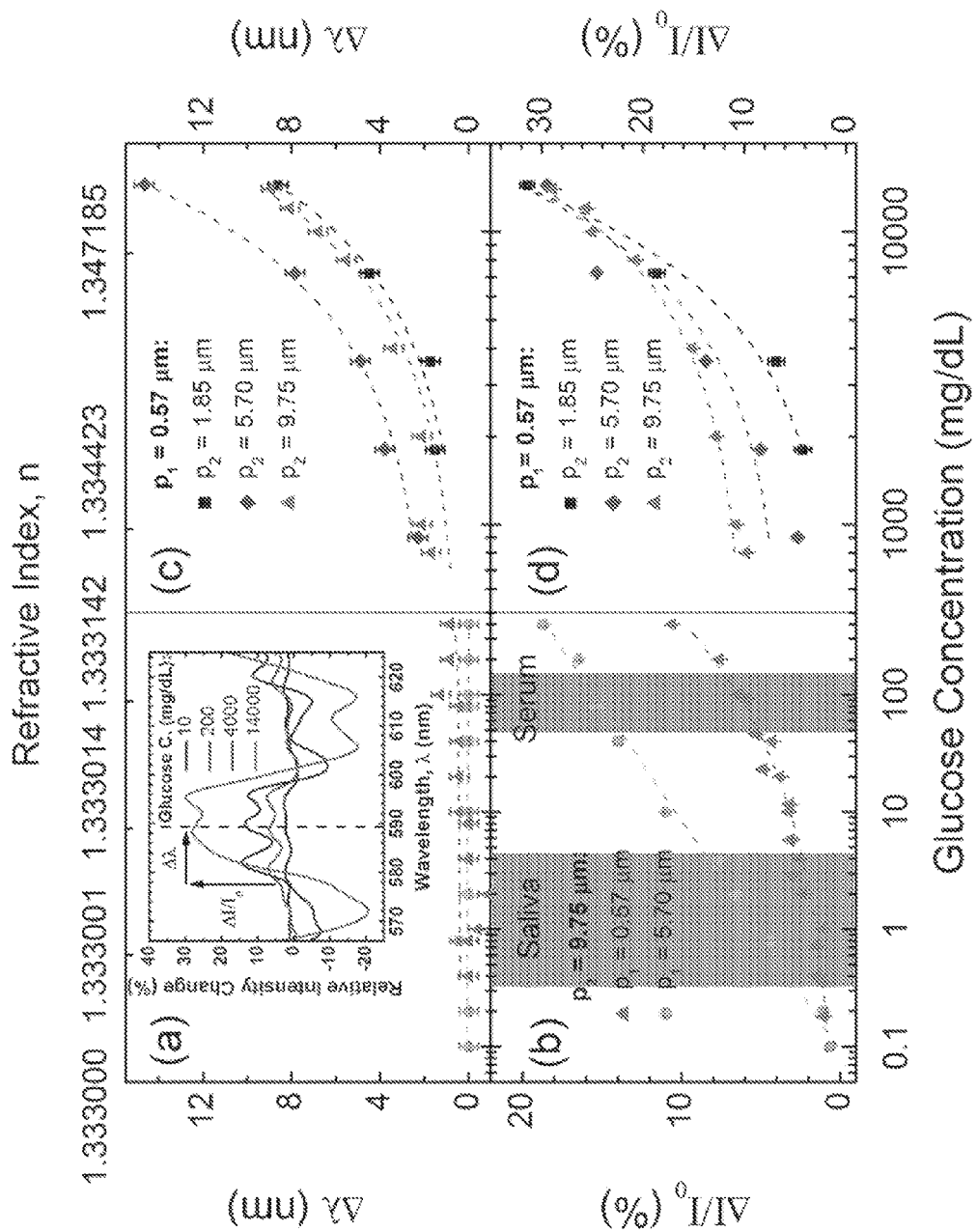
FIG. 14a-d show wavelength shift and relative intensity change versus glucose concentration, for four plasmonic interferometers, respectively.

FIG. 14 shows a sensing performance comparison at 590 nm for four devices, three of which have a constant $p_1=0.57$ μm and varying $p_2=1.85$, 5.70, and 9.75 μm, and the fourth with $p_1=5.70$ μm and $p_2=9.75$ μm. Panels a and c in FIG. 14 describe the wavelength shift, and panels b and d report the relative intensity change as a function of glucose concentrations, spanning 5 orders of magnitude, which correspond to a total refractive index change of only $\Delta_n=0.02$. The gray boxes in FIG. 14b highlight the physiological concentration ranges of glucose in saliva (lighter gray area) and serum (darker gray area), respectively. Typical physiological concentrations range between 0.36 and 4.3 mg/dL in saliva and 50 and 144 mg/dL in serum. The inset to FIG. 14a shows representative relative intensity change spectra for a device with $p_1=0.57$ μm and $p_2=9.75$ μm measured at four glucose concentrations. By monitoring the changes in the experimental spectra taken at different glucose concentrations, scattered data of $\Delta\lambda$ and $\Delta I/I_0$ can be obtained, as plotted in FIG. 14 for a wavelength of 590 nm. When panels a and b in FIG. 14 are compared, it is observed that, at low glucose concentrations (0.1-500 mg/dL), $\Delta\lambda$ does not show a significant change, whereas $\Delta I/I_0$ is a more reliable parameter for detection of glucose. At higher glucose concentrations (500-14 000 mg/dL) both $\Delta\lambda$ and $\Delta I/I_0$ can be used to detect the presence of glucose and quantify its concentration. The dashed lines are calibration curves obtained by least-squares fittings of the scattered experimental data points. The proposed plasmonic interferometers are able to sense the lowest glucose concentrations typically found in saliva.

At all concentrations, $\Delta I/I_0$ seems to outperform $\Delta\lambda$. In order to better quantify the device sensitivity, figures of merit can be calculated as the slopes of the calibration lines obtained by fitting $\Delta\lambda$ and $\Delta I/I_0$ data as a function of concentration. In particular, by dividing the wavelength shift $\Delta\lambda$ by the difference in the refractive index ($\Delta n$) between two glucose solutions we can define a figure of merit relative to the wavelength shift ($FOM_\lambda$) at each given concentration, i.e.

$$FOM_\lambda = \lim_{\Delta n \to 0} \frac{\Delta\lambda}{\Delta n}$$

Similarly, dividing the difference in the relative intensity change $\Delta I/I_0$ by $\Delta n$, the figure of merit relative to the intensity change ($FOM_I$) can be derived, at each concentration $$FOM_I = \lim_{\Delta n \to 0} \frac{\Delta I/I_0}{\Delta n}$$

The device with $p_1=0.57$ μm and $p_2=9.75$ μm (triangles) shows a $FOM_I$ of ~166 000%/RIU in the glucose concentration range typically found in saliva (0.2-8 mg/dL) and ~10 000%/RIU in the concentration range typically found in blood serum (40-400 mg/dL). For the device with longer $p_1=5.70$ μm (orange circles), the measured $FOM_I$ is even higher, reaching ~884 000 and ~17 000%/RIU in the glucose concentration ranges for saliva and serum, respectively. This device is able to detect a refractive index change as low as $3\times10^{-7}$ RIU. Experimentally, the relative intensity change is found to be a better figure of merit for detection of low glucose concentrations. The data suggest that at the lowest glucose concentrations, adsorption of glucose molecules directly onto the metal surface of the plasmonic interferometer determines an increased glucose concentration right at the device surface and higher $FOM_I$ than those simulated using a uniform glucose concentration in solution. Functionalization of the sample surface with linkers specific to glucose can further increase the device sensitivity and specificity. At higher glucose concentrations (500-14 000 mg/dL), $FOM_\lambda$ is between 370 and 630 nm/RIU for the three devices (FIG. 14c). The device with $p_1=0.57$ μm and $p_2=9.75$ μm, shows a decrease in $FOM_I$ from ~16 000%/RIU (FIG. 14b) to ~1000%/RIU (FIG. 14d), in agreement with the trend observed in the simulations, showing that plasmonic interferometers optimized for detection of low refractive index changes are indeed characterized by higher figures of merit at lower glucose concentrations. The measured figures of merit are at least 1 order of magnitude greater than what is reported in the literature, opening up the possibility to use plasmonic interferometers for detection of low concentrations of clinically relevant molecules. Moreover, the typical sensing volume of a plasmonic interferometer is only 20 fL, which corresponds to a sensed mass of 0.02 fg or ~67 000 molecules. If desired, sensing specificity can be achieved for multiple analytes by functionalizing the surface with antibodies that have high affinity to specific analytes.

Typical physiological concentrations range between 50-144 mg/dL in serum and between 0.36-4.3 mg/dL in saliva. The disclosed plasmonic interferometers are able to sense the lowest glucose concentrations typically found in saliva. Experimentally, a maximum sensitivity of ~32,000 nm/RIU and relative intensity change of ~105,000%/RIU were observed. These numbers are greater than those found in the literature (See Table 2 below). One proposed device according to aspects of the disclosure is able to detect as low as $3\times10^{-7}$ RIU, and it uses sensing volumes as small as 5 fL. These results demonstrate that plasmonic interferometers are candidates for the development of alternative optical sensors that can sense mass down to 0.02 fg, or ~67,000 molecules. The disclosed devices can therefore be used for the development of a minimal, non-invasive glucose measurement technique in saliva, which can greatly improve the lifestyle of diabetic patients.

Various experimental results suggest the possibility to detect analyte mass as low as 20 femtograms, by using various figures of merit, such as wavelength shift in the interference spectra and relative intensity change caused by a change in refractive index, determined by an increase in glucose concentration in solution.

Plasmonic Interferometry Coupled to Dye Chemistry for Specificity and Enhanced Sensitivity.

Figure 15:
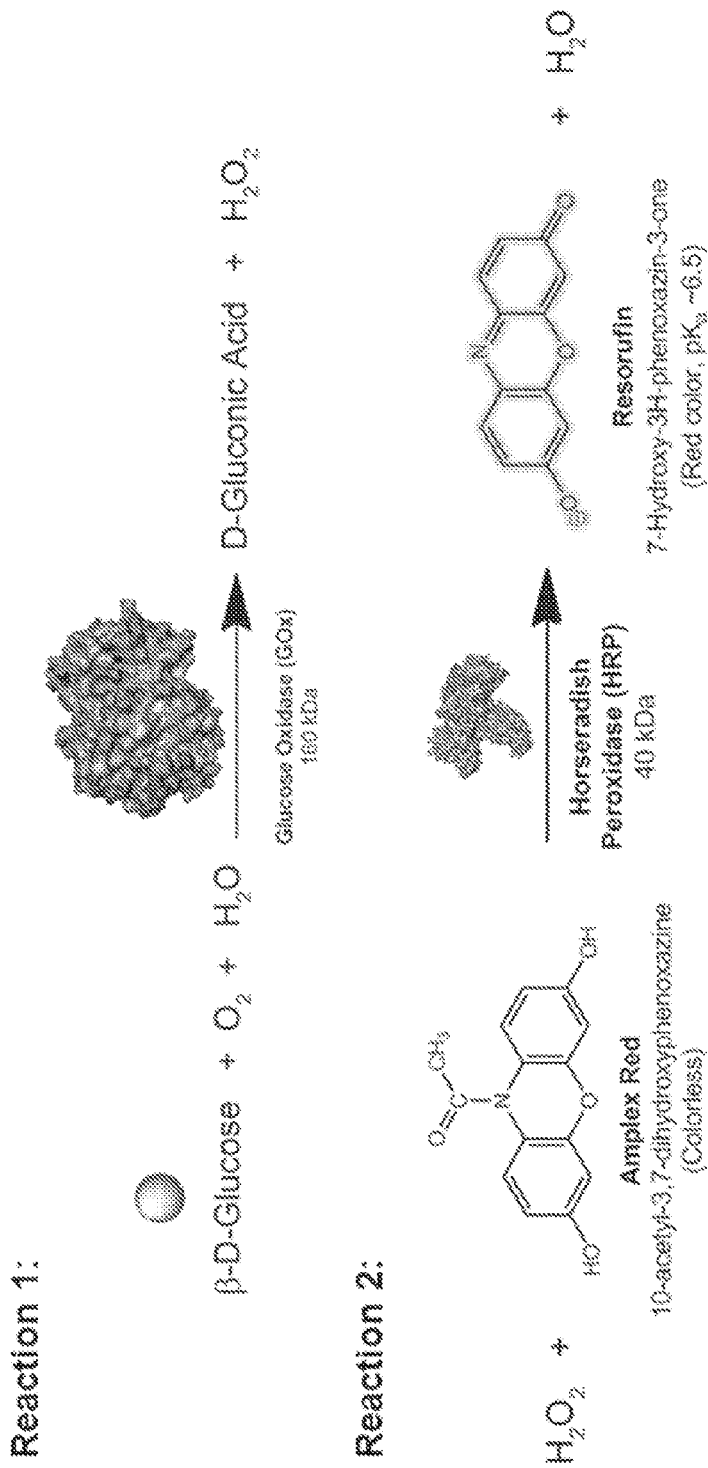
FIG. 15 shows the selective reaction scheme for glucose detection that utilizes the coupling of a chromogenic dye and plasmonic interferometry for enhanced selectivity and specificity.

According to aspects of the present invention, the sensor selectivity to glucose is improved using a proposed novel molecular recognition scheme that couples plasmonic interferometry with dye chemistry, specifically using 10-acetyl-3, 7-dihydroxyphenoxazine (Amplex Red). According to aspects of the present invention, glucose oxidase is added in solution to rapidly convert D-glucose into D-gluconolactone and $H_2O_2$ in a 1:1 stoichiometry $H_2O_2$ reacts with horseradish peroxidase (HRP) to oxidize Amplex Red into resorufin, a dye molecule which is characterized by a strong optical absorption coefficient at ~571 nm (see FIG. 15). The reaction can be monitored in real-time by simply measuring changes in the light intensity transmitted through the slit of each interferometer. As a result of the increased concentration of resorufin, the solution's refractive index and the absorption coefficient will increase, resulting in, respectively (1) a spectral shift in the interference conditions ($\Delta\lambda$), and (2) an intensity decrease due to increased SPP absorption ($\Delta I$). These two changes, ($\Delta\lambda$ and $\Delta I$) will provide information on the change in refractive index which can be directly correlated to the glucose concentration. The presence of β-D-Glucose in a reaction cocktail of glucose oxidase, horseradish peroxidase, and Amplex Red results in a red solution and in high absorbance that peaks at $\lambda$=572 nm.

Figure 16:
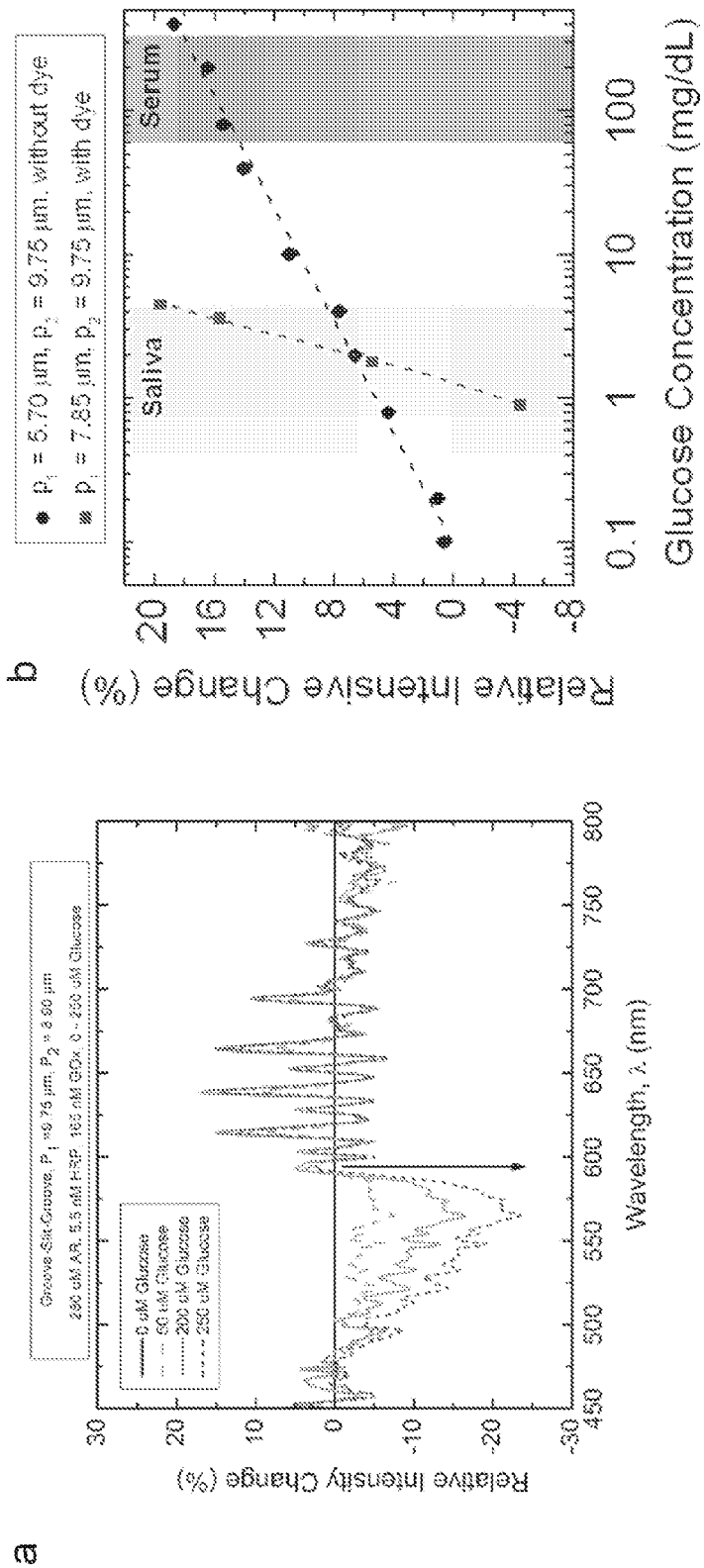
FIG. 16 shows (a) relative intensity changes based on a dye-coupled exemplary glucose detection method, according to aspects of the present disclosure; and (b) the calibration curve for this method comparing with the performance of a device not using the dye method.

According to aspects of the present invention, plasmonic interferometers are used for monitoring the kinetics of Amplex Red, glucose oxidase and glucose reaction. The effects of absorption using Amplex Red with a maximum absorbance at 572 nm on the spectral response of the plasmonic interferometer is shown in FIG. 16a. The absorption of the dye is directly proportional to the concentration of glucose above the sensing surface, as observed by the decrease in the relative intensity change between 500-600 nm. At wavelengths higher than 600 nm, there is a small wavelength shift due to the refractive index change caused by the increasing glucose concentration. The overall sensitivity is also observably higher than the plasmonic interferometer without dye present as seen in FIG. 16b. This approach demonstrates for the first time the enhanced specificity and selectivity of coupling the plasmonic interferometer with Amplex Red allowing for the development of point-of-care diagnostic tools for biomedical sensing of glucose and other clinically relevant analytes. The inventive matter involves the combining of plasmonic interferometry with dye chemistry as described. While certain specifics compounds are noted above (e.g. using glucose and 10-acetyl-3,7-dihydroxyphenoxazine (Amplex Red)), the general idea includes the use of dye chemistry to alter a molecular target as to optical absorption coefficient, refractive index and related optical characteristics.

Application of Plasmonic Interferometry to Trauma.

A plasmonic-based device that accurately measures, in real-time, the cytokine levels in polytrauma patients is provided. The demand for clinical testing of cytokine levels in serum has increased significantly because of their strong correlation to predicting the clinical course and outcome of trauma patients. This demand arises from the fact that a physician must make a decision on the timing and type of surgical treatment for a poly-trauma patient in the absence of real-time data. As such, these decisions are susceptible to human error, which can lead to systemic complications such as multi-organ dysfunction syndrome (MODS) and death of the patient. The physiological reaction to injury is most notably an inflammatory response that involves an interconnected network of protein mediators (cytokines, chemokines, nitric oxide) and effector cells (neutrophil, monocytes/macrophages and endothelial cells).

A controlled local inflammatory response is beneficial during the acute period following major trauma as the endogenous response systems modifies signaling pathways to limit further injury, prevent infection and initiate healing. When an exaggerated local inflammatory response propagates systemically, however, the result is known as a systemic inflammatory response syndrome (SIRS), which can lead to acute respiratory distress syndrome (ARDS), MODS and ultimately death.

In addition to initial injuries, long surgical procedures and fixation of fractures performed immediately after trauma induce surgical stress and can increase the risk of ARDS/MODS. About two decades ago, it was believed that surgical stabilization of all fractures had to be performed within 24 hours after injury. However, this paradigm is under heavy scrutiny as new technologies enable us to further elucidate the mechanism behind the development of ARDS/MODS.

The "second-hit" phenomenon theory suggests that a patient in a hyper-inflammatory physiologic state following an initial injury (first hit) may be pushed over a threshold for the development of MODS by an ill-timed surgical procedure (second hit). Surgeons have noted that a focus on resolving hemorrhage and stabilizing high-priority injuries in the first 72 hours, and thereby delaying extensive orthopedic procedures, can greatly improve the chance of patient survival. The approach of staging surgical intervention is known as damage control orthopedics (DCO). In order for DCO to gain widespread implementation, a standardized set of guidelines to base clinical decisions regarding the appropriate timing and extent of surgical intervention in a poly-trauma patient is required.

One method for differentiating those patients who are ready and can tolerate prolonged surgical procedures is to monitor their cytokine response. The systemic release of inflammatory cytokines such as TNF-α (Tumor Necrosis Factor-alpha, involved in the acute phase response), or the interleukins IL-1, IL-6 and IL-8 is proportional to the severity of trauma, surgical stress response and sepsis. Elevated IL-6 and IL-8 levels have been found to increase significantly in patients in hemorrhagic shock and in 95% of patients undergoing routine surgical procedures. The major limitation in the accuracy of measuring cytokine levels lies in their inherent short half-lives ranging from approximately 6 minutes for IL-1 and 20 minutes for TNF-α.

Currently, cytokine levels in blood serum is predominantly quantified by immunoassay such as commercially available enzyme-linked immunosorbent assays (ELISA), radioimmunoassay and immunoaffinity column assays. Common amongst these laboratory techniques is the need for incubation (2-3 hours) and the subsequent delay in the diagnosis. Recently, optical sensors based on Surface Plasmon Resonance (SPR) technology such as the Biacore® have been used to monitor cytokine concentrations in real time and without labeling. However, these machines are bulky, expensive and require highly qualified personnel to operate.

In one aspect, a device capable of quantifying markers of inflammation in serum in real-time is described. The device provides physicians with the ability to assess the type and timing of surgery that would reduce the impact of the second hit insult. The device based on novel plasmonic architecture can accurately and rapidly measure the level of cytokines in blood serum in real-time. Cytokine levels reflect the severity of injury in a patient. The disclosed invention provides a new method for measuring cytokine levels in patients suffering from traumatic injury (e.g., American soldiers, victims of vehicular impact).

Under aspects of the present disclosure, the provided inventive plasmonic interferometer allows for multiplex, real-time quantification of cytokines in addition to surmounting all of the afore-mentioned limitations. The sensitive biological element consists of cytokines in blood serum, delivered using micro-fluidic techniques.

According to alternative aspects of the present disclosure, methods of device fabrication and optimization for effective cytokine detection in blood serum are provided.

According to alternative aspects of the present disclosure, methods of development and implementation of surface chemistry by which to attach selective sensing elements for targeted cytokines are provided. Table 1 lists major cytokines involved in trauma.

TABLE 1

Major inflammatory cytokines involved in trauma.[1]

| Major cytokines | Molecular Mass | The role of cytokines |
| --- | --- | --- |
| Tumor necrosis factor-α (TNF-α) | 17.5 kDa | Potential marker of inflammation[a] |
| Interleukin-1 (IL-1) | 18 kDa | Elaboration and release of other cytokines during immune response[b] |
| Interleukin-6 (IL-6) | 20.3 kDa | Reliable marker of the severity of injury, magnitude of systemic inflammation, and mortality rate[c] |
| Interleukin-8 (IL-8) | 8.3 kDa | Determinant of postinjury mortality in pediatric blunt-trauma patients[d] |
| Interleukin-10 (IL-10) | 18.8 kDa | Down-regulation of pro-inflammatory cytokines[e] |

[1]References:
[a]Giannoudis P V, Injury 34, 397-404 (2003);
[b]Sutton C, The Journal of Experimental Medicine 203, 1685-1691 (2006);
[c]Mimasaka S, Injury 38, 1047-1051 (2007); Hack C E, Blood 74, 1704-1710 (1989); Gebhard F, Arch Surg 135, 291-295 (2000);
[d]Ozturk H, Pediatr Surg Int 24, 235-239 (2008);
[e]Pastores S M, Acad Emerg Med 3, 611-622 (1996).

According to alternative aspects of the present disclosure, a plasmonic interferometer used for the rapid, accurate, and low-cost measurement of cytokines can significantly improve the outcome of triage at an emergency center. The real-time sensing capability of the plasmonic interferometer can also help elucidate pro- and anti-inflammatory release mechanisms needed to verify the second hit phenomenon. Our plasmonic interferometers have the potential to become an invaluable point-of-care diagnostic tool for orthopedics surgeons to monitor the evolution of clinical cytokines and guide them in making informed decisions to treat and operate on patients affected by polytrauma, preventing the onset of MODS.

Figure 17:
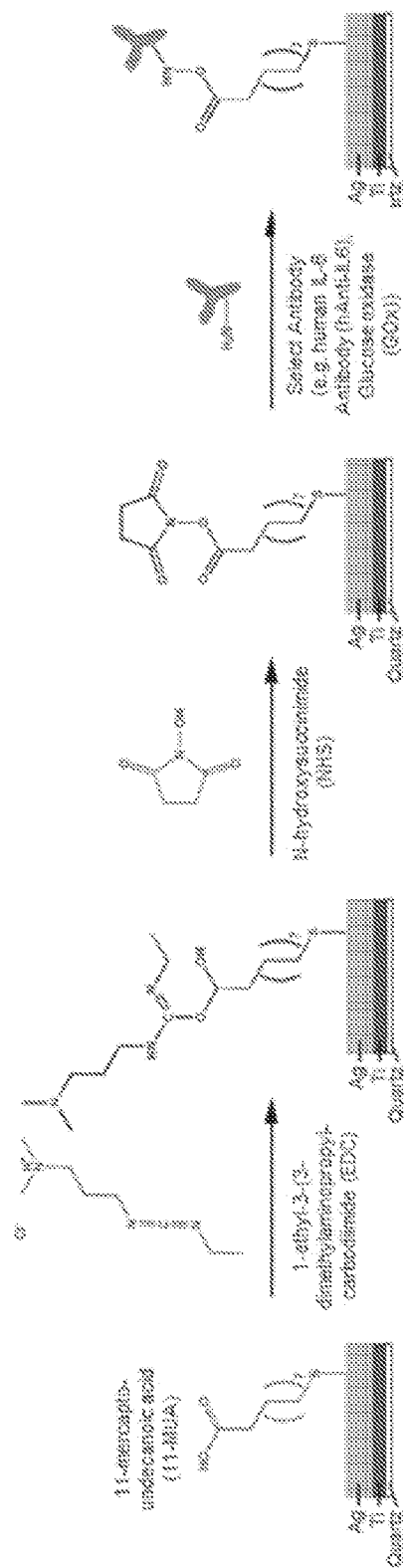
FIG. 17 shows a schematic for immobilization of a selective protein to a targeted analyte (e.g. human anti-IL6 (hAnti-IL6 for cytokine detection, glucose oxidase (GOx) for glucose detection, etc.) onto a metal substrate that supports surface plasmon generation (e.g. Ag, Au, etc.) using EDC/NHS coupling.

Immobilization of Antibodies and Capture Proteins Specific to Targeted Cytokines and Other Biochemical Analytes Under alternative aspects of the present disclosure, chemistry methods are provided for optimally modifying the surfaces of the plasmonic interferometers. For example, FIG. 17 shows a schematic for human anti-IL6 (hAnti-IL6) or other capture proteins immobilized onto Au (Ag) substrates using EDC/NHS coupling.

As a starting point, substrates were prepared from clean quartz measuring one square inch. An adhesive layer (4 nm) of either titanium (Ti) or chromium (Cr) was e-beam deposited onto the quartz followed by e-beam deposition of a thin layer (300 nm) of either gold (Au) or silver (Ag). The resulting metal-coated quartz was immersed in an ethanol solution containing 1 mM 11-mercaptoundecanoic acid (11-MUA) and incubated overnight at room temperature. After rinsing the substrate with copious amounts of ethanol followed by acetone, the substrate was immersed in an aqueous solution containing 5 mM 1-ethyl-3-(3-dimethylaminopropyl)carbodiimide (EDC) and 5 mM N-hydroxysuccinimide (NHS) for 4 h to generate a reactive ester at the terminus of the self-assembled monolayer. The substrate was rinsed with de-ionized water to remove any unreacted EDC or NHS prior to its exposure to an aqueous solution containing hAnti-IL6 (8 μg/mL) for 18 h. The ensuing chemical reaction insures that IL-6 is covalently attached to the substrate surface via amide bond formation between the primary amine group on IL-6 and the reactive ester of 11-MUA. Prior to FTIR analysis, the substrate was rinsed with de-ionized water and dried under nitrogen.

Figure 18:
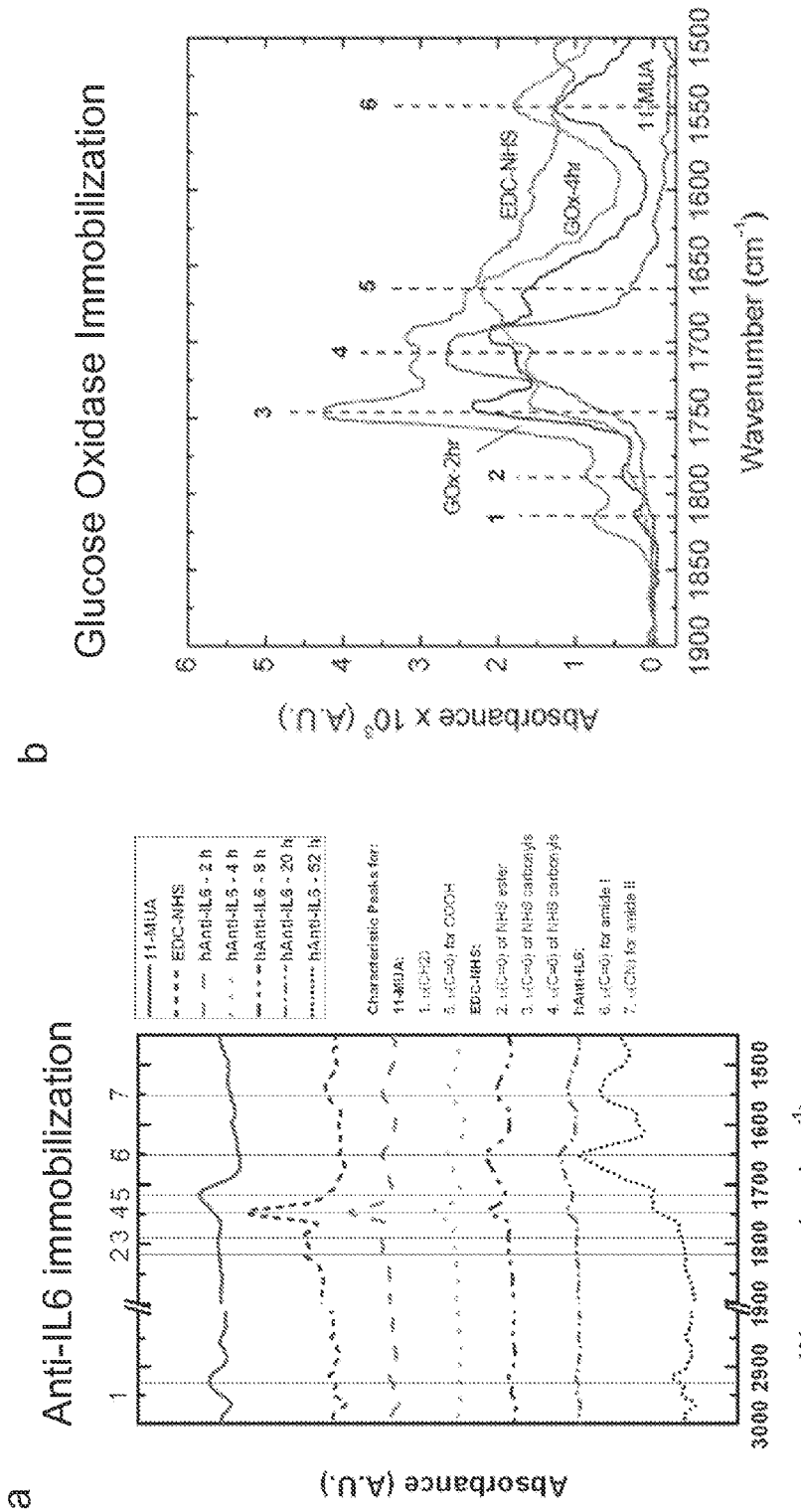
FIG. 18a shows the temporal evolution of human anti-IL6 antibody (hAnti-IL6) immobilized onto gold-coated quartz substrate via EDC/NHS coupling chemistry (11-MUA=thiol coupling agent, EDC/NHS=free coupling agent, Anti-ILS=coupled human anti-IL6 antibody)
FIG. 18b shows temporal evolution of glucose oxidase (GOx) monolayer immobilized onto a silver-coated quartz substrate via EDC/NHS coupling chemistry.

Surface modification on a gold-coated quartz substrate was performed and infrared spectra of the immobilization process of hAnti-IL6 were collected on a Nicolet Nexus 670 FTIR spectrometer. FIG. 18a shows sequential infrared spectra of hAnti-IL6 immobilized onto gold-coated quartz substrate via EDC/NHS coupling chemistry. The specular reflectance was measured and converted to absorbance. Seven characteristic absorbance peaks are labeled with bold numbers in FIG. 18a: (1) asymmetric stretch of $CH_2$ at 2950 $cm^{-1}$; (2) NHS esters stretching mode at 1815 $cm^{-1}$; (3) symmetric stretch of NHS carbonyls at 1750 $cm^{-1}$; (4) symmetric stretch of NHS carbonyls at 1740 $cm^{-1}$; (5) carbonyl stretching of the carboxylic acid groups (—COOH) of 11-MUA at 1710 $cm^{-1}$; (6) carbonyl stretching mode corresponding to the amide bonds (amide I) in hAnti-IL6 at 1675 $cm^{-1}$; and (7) a combination of N—H bending and C—N stretching modes of the amide bonds (amide II) in hAnti-IL6 at 1550 $cm^{-1}$. The amide I and amide II peaks (see FIG. 18a: peaks 6 and 7, blue line) are indicative that hAnti-IL6 was immobilized onto the gold-coated quartz substrate. The same immobilization scheme can be applied for the immobilization of other capture proteins such as glucose oxidase (GOx) as seen in FIG. 18b.

FIG. 18a shows evidence of surface functionalization using hAnti-IL6 immobilization on a metal surface. Increasing the immobilization time leads to an increase in the surface coverage (FIG. 18a); the measurements evidence a continuous, uniform monolayer of hAnti-IL6 covalently bound at the surface.

Under alternative aspects of the present disclosure similar procedures can modify plasmonic interferometers with the other targeted cytokines and other analytes of interest. Further characterization of the modified surfaces can include antibody staining, contact angle measurements, and collection of X-ray photoelectron spectra to insure the coatings are homogeneous over the entire surface of the substrate.

Figure 19:
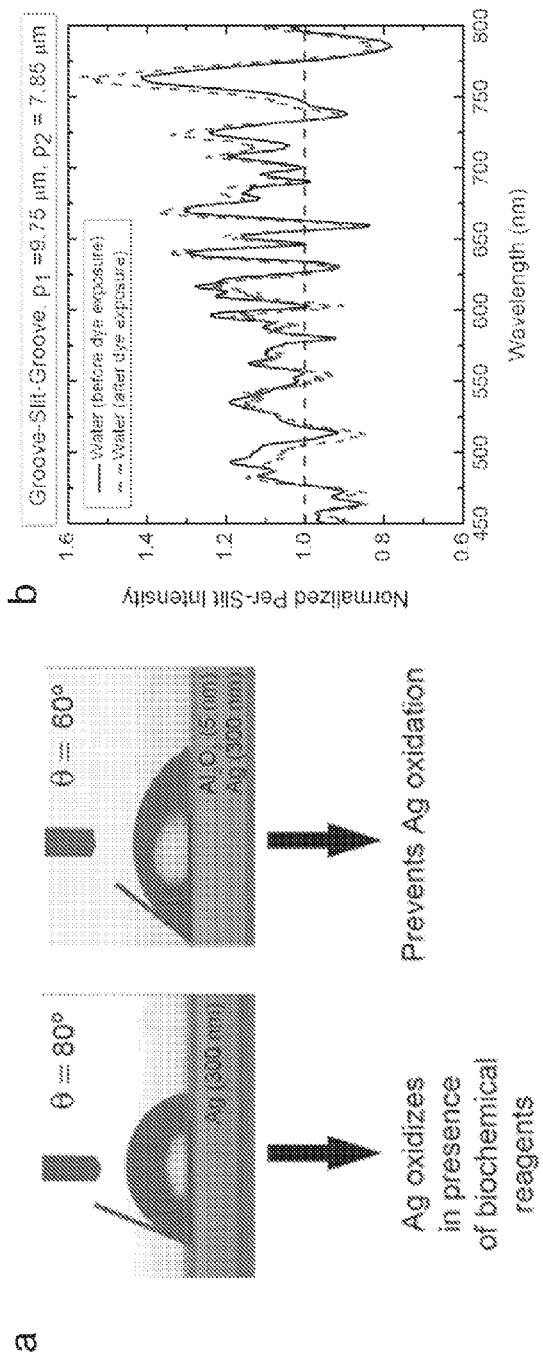
FIG. 19 shows (a) the contact angles for the silver film with and without Al$_2$O$_3$ protection; and (b) the normalized transmitted intensity in water for a device protected by the Al$_2$O$_3$ film before and after the dye exposure, according to aspects of the present disclosure.

Under alternative aspects of the present disclosure, protection of the metal surface (in particular Ag) from oxidation from biochemical reagents and buffers, a thin film of aluminum oxide ($Al_2O_3$), silicon dioxide ($SiO_2$) and the like can be deposited on top of the metal surface. This causes the surface to become more hydrophilic in the case of Ag and $Al_2O_3$ (see FIG. 19a). Furthermore, this method enables the chip to be reused subsequent to chemical dye or other reagent exposure, as indicated by the return of the peak positions at the same wavelengths observed in FIG. 19b.

Device Integration and Prototype Designs.

Figure 20:
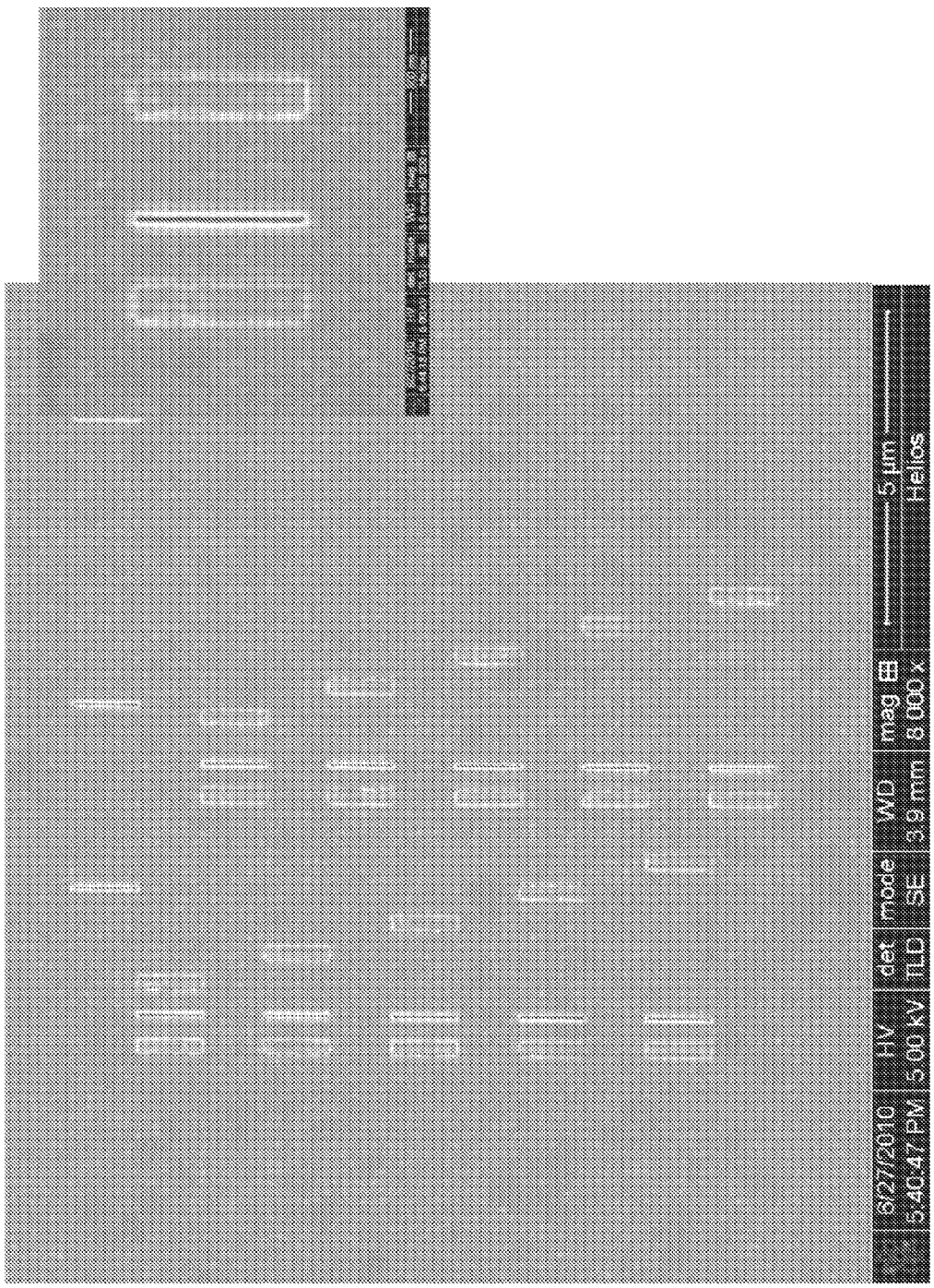
FIG. 20 shows an exemplary arrangement of plasmonic interferometers in an array, according to aspects of the present disclosure.

FIG. 20 shows an implementation of ten 1 μm-long interferometers in an area of 77 μm², demonstrating an array density of 13 million devices per square centimeters. The individual interferometers are arranged in columns and are spaced in a way to minimize the surface plasmon interference between neighboring interferometers of adjacent columns.

Fabrication of several plasmonic interferometers on the same chip enable fast characterization of the optical response as a function of the above mentioned geometric parameters, and further can allow for a comparison with simulation results enabling high-throughput experiments.

Figure 21:
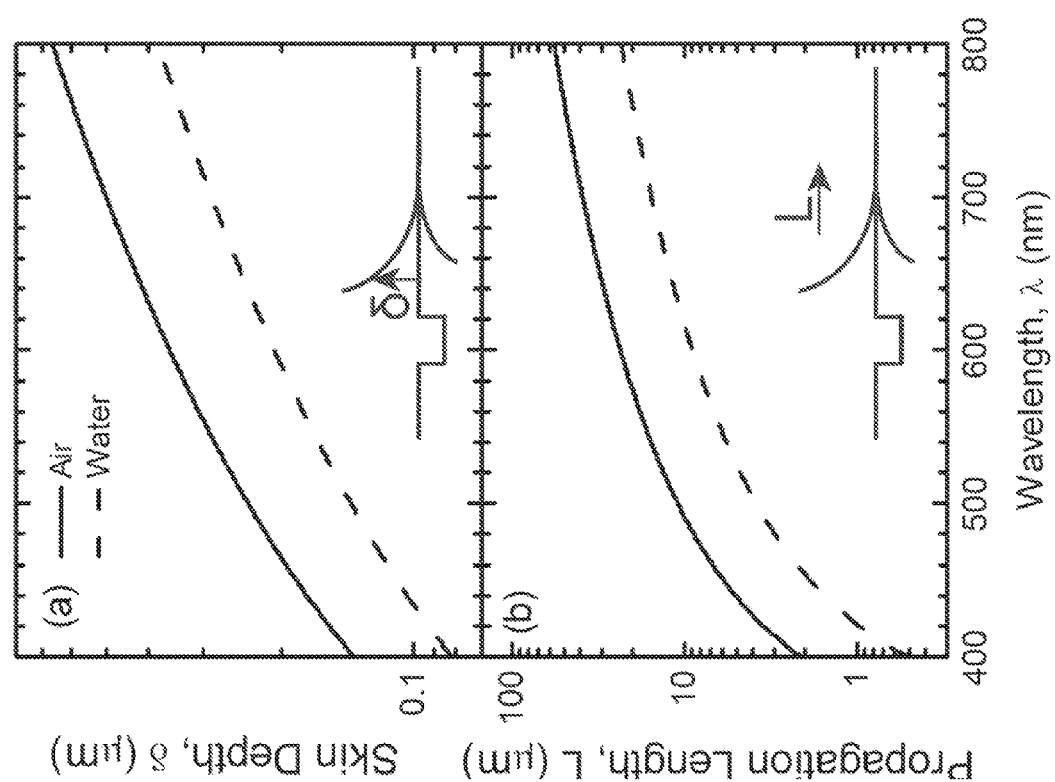
FIGS. 21a-b show the skin depth and propagation length of surface plasmons, respectively, according to aspects of the present disclosure.

FIG. 21a shows how the skin depth and propagation length of surface plasmons vary for different wavelengths, for two fluids: water and air. The propagation length is defined as the distance that a surface plasmon should propagate for its intensity to decay by a factor of 1/e. For example, in FIG. 21b, at λ=500 nm, the propagation length is about 3 μm. Between two neighboring interferometers, a separation distance equal to two propagation lengths adequately provides sufficient isolation between the two neighboring interferometers. For each propagation length there is an exponential decay of the surface plasmon intensity. Other ways to provide optical isolation between neighboring interferometers can include, for example, deposition of platinum or chromium. Platinum and chromium have strong absorption characteristics, therefore surface plasmons lose their intensity when they propagate through them. Platinum and chromium can be deposed using standard thin-film deposition techniques. The thin film can be as long as the slit of the neighboring interferometer and have a width, for example, of 1 μm. The thickness of the thin film can vary between 2 nm and 3 nm.

Under alternative aspects of the present disclosure, a hand-held device is provided. The hand-held device can be configured with a microarray of plasmonic interferometers with surfaces chemically modified to capture specific analytes found in bodily fluids. For example, a sub-microliter sample of serum can be introduced to the interferometer chamber through capillary action. Subsequent to photonic detection, the data can be displayed, for example, on a LCD display. Specific recognition of targeted molecules eliminates the need for extensive extraction and/or purification of the sample. Additionally, the integration of the microarray detector with MEMS technology can enable the construction of a biochemical photonic sensor that can be mass produced at low cost.

Figure 22:
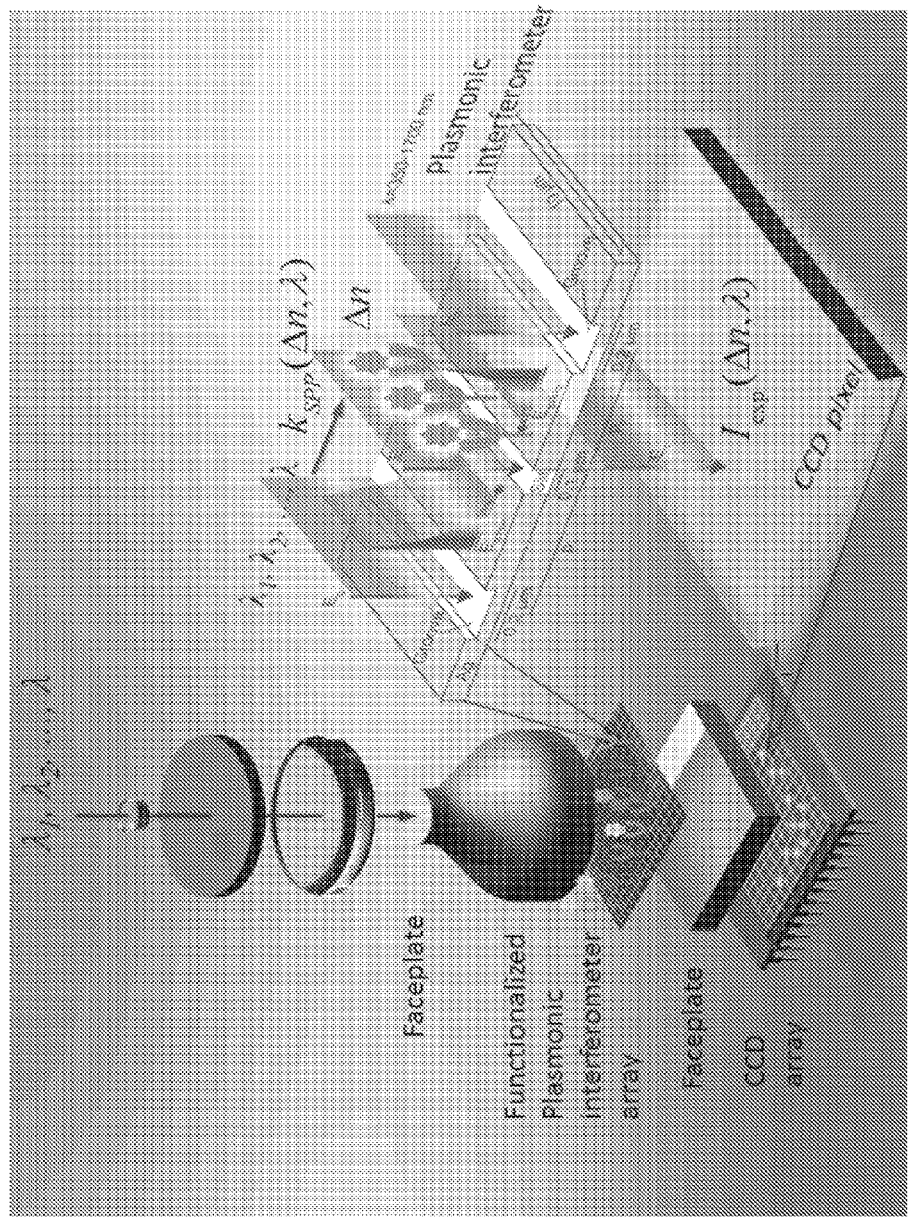
FIG. 22 shows a three-dimensional computer-aided design and rendering of a chip with plasmonic interferometers used in detecting multiple analytes, according to aspects of the present disclosure.

Under alternative aspects of the present disclose, typical interferometer dimension and separation distances can be scaled down by use of nano-imprint lithography in order to fabricate and integrate as many as one million interferometers per centimeter squared on a metal film for improved sensor throughput, which would be desirable, for example, for faster drug screening and discovery. A device according to aspects of the present disclosure is shown schematically in FIG. 22. A sub-microliter sample of analyte in solution can be introduced to the interferometer chamber through capillary action (not shown) comprising inlet and outlets for positioned to permit inflow and outflow of a second fluid in the sample holder. By varying the normal incident wavelength, each CCD pixel can record the normalized transmission spectrum through an individual plasmonic interferometer. Flow of the analyte in solution and further binding to the specific linker will produce a shift in the spectrum. Subsequent analysis in situ will determine calibration curves. Therefore, the proposed sensor can detect the refractive index change at various wavelengths simultaneously. Additionally, the CCD camera integrated on the back of our sensor chip will allow multiplexed, real-time detection of light transmitted through each and every plasmonic interferometer, thus enabling individual addressability and multispectral imaging capabilities to collect 2D maps in a single reading. A CMOS sensor can alternatively be used to record the light through each individual plasmonic interferometer.

This can result to high-throughput measurements of concentration and type of analytes (selected according to specific linkers) for monitoring several patients simultaneously. For example, by employing linkers specific to different analytes, and using 1,000 plasmonic interferometers in parallel, a multiplexed screening of various biochemical analytes for 30+ patients can be accomplished in one run.

FIG. 23a shows a prototype schematic of a glucose monitor, according to aspects of the present disclosure. FIG. 23b shows an actual photograph of the prototype 2300. The prototype consists of a biochip 2301, an integrated plasmonic sensor array chip 2302, an LCD display 2303, a microfluidic channel 2304, and an integrated light source. The prototype also consists of an optical meter, which is a point-of-care, battery-powered, cube-shaped device that opens and closes with a flex-hinge. When opened, the top panel is a LCD screen that serves both as a display panel and a light source used for optical sensing. The bottom panel contains a hidden CCD camera located directly underneath a recess for which the biochip can be placed. The camera is responsible for recording the intensity change for each interferometer at its corresponding pixel locations. The biochip comprises a plurality of plasmonic interferometers and can be packaged individually.

Figure 24:
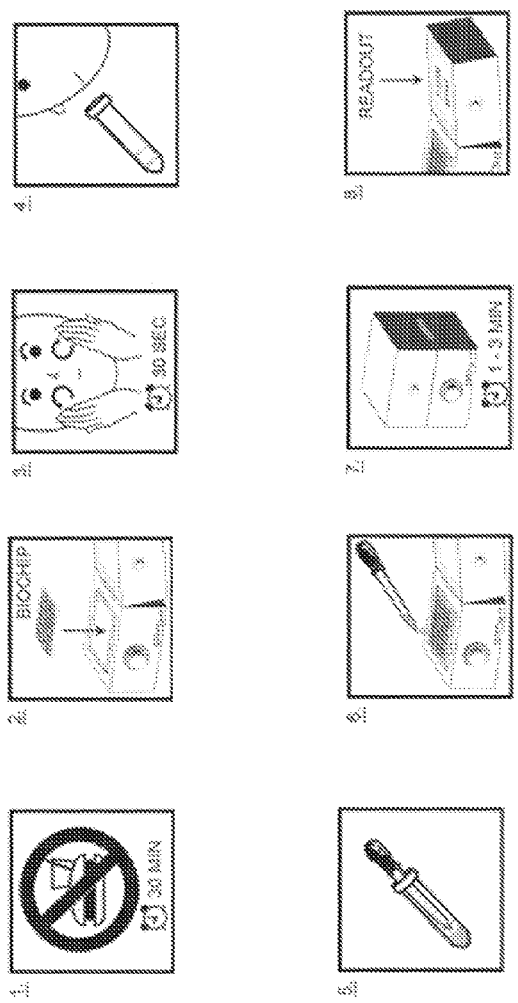

In other embodiments, a kit is provided for operation of a glucose test. The kit includes chemicals necessary for reaction with saliva sample for generation of dye indicator, e.g., horseradish peroxidase, glucose oxidase and 10-acetyl-3,7-dihydroxyphenoxazine (Amplex Red) and instructions for use in the detection of glucose in saliva using a plasmonic interferometer device. FIG. 24 is a graphical illustration of the instructions to operate the testing glucose monitor.

What is claimed is:

1. A system for detecting an analyte comprising:
   a plasmonic interferometer, the plasmonic interferometer comprising a first surface and a second surface on an opposite side of the plasmonic interferometer than the first surface, the first surface having a first groove and a second groove and a slit disposed between the first groove and the second groove to define a first distance between the slit and the first groove and a second distance between the slit and the second groove, wherein the first and second distances are selected to provide interference of light at the slit;
   a light source for illuminating the first surface of the plasmonic interferometer;
   a detector for detecting light transmitted through the slit, the detector positioned proximate to the second surface of the plasmonic interferometer; and
   a sample holder for disposing a sample to be analyzed onto the first surface of the plasmonic interferometer.

2. The system of claim 1, wherein the first and second scattering elements are surface plasmon polariton scattering elements.

3. The system of claim 1, wherein the aperture slit is designed to allow collection of a light property.

4. The system of claim 1, wherein the plasmonic interferometer comprises a conductive film.

5. The system of claim 4, wherein the plasmonic interferometer comprises one of gold (Au), silver (Ag), aluminum (Al), copper (Cu), or other noble metal, and a functional protective layer such as indium-tin oxide (ITO), or silicon dioxide, or other functional material.

6. The system of claim 1, wherein the sample holder comprises walls positioned to retain the sample on the first surface of the plasmonic interferometer.

7. The system of claim 1, wherein the sample holder comprises a microfluidic channel positioned to direct a sample over the first surface of the plasmonic interferometer.

8. The system of claim 1, wherein the first surface of the plasmonic interferometer is functionalized with an analyte capture agent selected to capture the analyte to be detected.

9. The system of claim 1, wherein the first surface of the plasmonic interferometer is coated with a dielectric material.

10. The system of claim 1, wherein the first surface of the plasmonic interferometer is coated with an analyte capture agent selected to capture the analyte to be detected.

11. The system of claim 1, wherein the analyte capture agent is selected to capture cytokines.

12. The system of claim 1, further comprising a power source.

13. The system of claim 1, wherein the detector is a CCD camera.

14. The system of claim 1, wherein the detector is a CMOS camera.

15. The system of claim 1, wherein the detector is external.

16. The system of claim 1, wherein the detector is internal.

17. The system of claim 1, wherein the first scattering element and the second scattering element have a length between 10 nm and 100 μm.

18. The system of claim 1, wherein the first scattering element and the second scattering element have a width between 10 nm and 500 nm.

19. The system of claim 1, wherein the first and the second scattering element have a depth between 1 nm and 300 nm.

20. The system of claim 1, wherein the aperture has a width between 50 nm and 500 nm.

21. The system of claim 1, wherein the second distance is greater than the first distance.

22. The system of claim 1, wherein the second distance is equal to the first distance.

23. The system of claim 1, wherein the light source is selected to provide light at optical frequencies.

24. The system of claim 1, further comprising a protective layer of a dielectric material, or a functional layer, or oxidative dye, or chromogenic dye disposed on the first surface.

25. The system of claim 1, wherein the first scattering element and the second scattering element are linear.

26. The system of claim 1, wherein the first scattering element and the second scattering element are arcs.

27. The system of claim 1, wherein the aperture is a hole.

28. The system of claim 1, wherein the first scattering element and the second scattering elements are curvilinear.

29. The system of claim 1, further comprising inlet and outlets positioned to permit inflow and outflow of a second fluid in the sample holder.

30. The system of claim 1, wherein the first and second scattering elements comprise a plurality of scattering elements of different sizes, shapes and/or dimensions, and the aperture comprises several slits of different sizes, shapes and/or dimensions.

31. A method of real-time detection of an analyte comprising:
providing a plasmonic interferometer according to claim 1
applying a sample to be analyzed on the first surface of the plasmonic interferometer;
illuminating the plasmonic interferometer with the light source;
measuring a light property of a composite light transmitted through the aperture; and
determining a characteristic of an analyte of interest based on the measured light intensity;
wherein the composite light is generated through interference at the aperture of the incident light and scattered light from the first and second scattering elements.

32. The method of claim 31, wherein the step of measuring a light property includes measuring a light intensity of the composite light transmitted through the aperture.

33. The method of claim 31, wherein a first wave of scattered light propagates from the first scattering element to the aperture;
a second wave propagates from the second scattering element to the aperture; and
wherein the first and second distances are selected to provide constructive interference of the first and second light.

34. A method of real-time detection of an analyte comprising:
providing a plasmonic interferometer according to claim 1;
applying a sample to be analyzed on the first surface of the plasmonic interferometer, wherein the sample comprises an oxidative or chromogenic dye selected to absorb particular light frequencies;
illuminating the plasmonic interferometer with the light source;
measuring a light property of a composite light transmitted through the aperture; and
determining a characteristic of an analyte of interest based on the measured light intensity;
wherein the composite light is generated through interference at the slit of the incident light and scattered light from the first and second scattering elements.

35. A method of spectroscopic measurements of the dispersion relation and optical constants of dielectric materials in gaseous, liquid, or solid form, the method comprising:
providing a plasmonic interferometer according to claim 1;
applying a sample to be analyzed on the first surface of the plasmonic interferometer, wherein the sample comprises at least one of a dielectric material and a mixture of dielectric material;
illuminating the plasmonic interferometer with a light source;
measuring a light property of a composite light transmitted through the aperture; and
determining a characteristic of an analyte in the sample based on the measured light property;
wherein the composite light is generated at the aperture through interference of incident light from the source and scattered light from the first and second scattering elements.

36. A system for detecting a plurality of analytes comprising:
a plurality of plasmonic interferometers, each plasmonic interferometer comprising:
a first surface and a second surface on an opposite side of the plasmonic interferometer than the first surface, the first surface having a first groove and a second groove; and
a slit disposed between the first groove and the second groove to define a first distance between the slit and the first groove and a second distance between the slit and the second groove;
wherein the first and second distances are selected to provide controlled interference of light at the aperture slit;

a light source for illuminating the first surface of each of the plurality of plasmonic interferometers;

a plurality of detectors for detecting light transmitted through the slit of each plasmonic interferometer, each detector positioned proximate to the second surface of a corresponding plasmonic interferometer; and a plurality of sample holders, each sample holder disposing a sample to be analyzed onto the first surface of each plasmonic interferometer.

37. The system of claim 36, wherein the number of plasmonic interferometers varies between 1 and 10,000,000,000.

38. The system of claim 36, wherein the plasmonic interferometers are etched over an area that varies between 1E-6 mm$^2$ and 1E4 mm$^2$.

39. The system of claim 36, wherein two neighboring plasmonic interferometers are separated by a distance of at least two propagation lengths.

40. The system of claim 36, wherein two neighboring plasmonic interferometers are separated by a thin film of platinum or chromium.

41. The system of claim 36, wherein neighboring plasmonic interferometers are optimally staggered to minimize cross-talk along the plane.

42. A system for detecting an analyte comprising:

a plasmonic interferometer, the plasmonic interferometer comprising a first surface and a second surface on an opposite side of the plasmonic interferometer than the first surface, the first surface having a first groove and a second groove and a slit disposed between the first groove and the second groove to define a first distance between the slit and the first groove and a second distance between the slit and the second groove, wherein the first and second distances are selected to provide interference of light at the slit;

a light source for illuminating the first surface of the plasmonic interferometer;

a detector for detecting light transmitted through the slit, the detector positioned proximate to the second surface of the plasmonic interferometer; and a sample holder for disposing a sample to be analyzed onto the first surface of the plasmonic interferometer;

wherein the sample comprises an oxidative or chromogenic dye selected to absorb particular light frequencies.

* * * * *